US 8,165,660 B2

(12) United States Patent
Pfister et al.

(10) Patent No.: US 8,165,660 B2
(45) Date of Patent: Apr. 24, 2012

(54) SYSTEM AND METHOD FOR SELECTING A GUIDANCE MODE FOR PERFORMING A PERCUTANEOUS PROCEDURE

(75) Inventors: Marcus Pfister, Bubenreuth (DE); Norbert Strobel, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 405 days.

(21) Appl. No.: 12/431,518

(22) Filed: Apr. 28, 2009

(65) Prior Publication Data
US 2009/0274271 A1 Nov. 5, 2009

Related U.S. Application Data

(60) Provisional application No. 61/049,803, filed on May 2, 2008.

(51) Int. Cl.
*A61B 6/00* (2006.01)
*A61B 19/00* (2006.01)
*G03B 42/02* (2006.01)

(52) U.S. Cl. ........ 600/427; 600/424; 600/429; 606/130; 378/62; 378/68; 378/69; 378/205; 378/206

(58) Field of Classification Search .................. 600/427, 600/429, 424; 606/130; 378/206, 68, 69
See application file for complete search history.

(56) References Cited

U.S. PATENT DOCUMENTS

| | | | |
|---|---|---|---|
| 5,782,842 A * | 7/1998 | Kloess et al. | 606/130 |
| 6,195,577 B1 * | 2/2001 | Truwit et al. | 600/427 |
| 6,811,313 B2 | 11/2004 | Graumann et al. | |
| 2006/0039537 A1 | 2/2006 | Strobel | |
| 2006/0120507 A1 | 6/2006 | Brunner et al. | |
| 2007/0255292 A1 | 11/2007 | Pfister | |
| 2008/0089467 A1 | 4/2008 | Lauritsch et al. | |
| 2008/0194945 A1 | 8/2008 | Kukuk et al. | |
| 2008/0200876 A1 | 8/2008 | Kukuk et al. | |

OTHER PUBLICATIONS

Wood et al. Technologies for Guidance of Radiofrequency Ablation in the Multimodality Interventional Suite of the Future. J Vasc Interv Radiol. Jan. 2007 ; 18(1 Pt 1): 9-24. doi:10.1016/j.jvir.2006.10.013.*

* cited by examiner

*Primary Examiner* — Brian Casler
*Assistant Examiner* — Phong K Huynh
(74) *Attorney, Agent, or Firm* — Alexander J Burke

(57) ABSTRACT

A system for planning a percutaneous procedure provides a patient 3-dimensional image data set within which an instrument trajectory is defined, for example, by selecting a skin entry point and a target point. A line, or "planned path," is generated between the points. The system determines whether the path can be targeted so an optical axis of a movable arm coincides with the path so that a laser can be used for instrument guidance or whether a planned path can be targeted so that a C-arm can be made to coincide with the path so that the extension of the path is projected onto a radiation detector, using x-ray radiation. If neither laser guidance or x-ray guidance can be used, the path is replanned.

24 Claims, 18 Drawing Sheets

SYSTEM AND METHOD FOR SELECTING A GUIDANCE MODE FOR PERFORMING A PERCUTANEOUS PROCEDURE

CROSS-REFERENCE TO RELATED APPLICATIONS

This is a U.S. non-provisional application of U.S. provisional patent application Ser. No. 61/049,803, filed May 2, 2008, by Marcus Pfister, et al., titled "Workflow for Percutaneous Procedures," the entirety of which application is incorporated herein by reference.

FIELD OF THE DISCLOSURE

The disclosure relates generally to methods for planning and performing percutaneous procedures, and more particularly to methods for automatically aligning medical devices to perform percutaneous procedures that reduce overall radiation exposure to patient and user.

BACKGROUND

With modern angiography systems, it is possible to obtain not only 2-dimensional (2D) fluoroscopic images but, by rotation of a C-arm around the patient, 3-dimensional (3D) CT-like images. For the purpose of intervention planning or navigation, these 3D datasets can be co-registered with the 2D fluoroscopic image. This registration can be used to plan percutaneous puncture procedures, such as needle biopsies. Once registered, 2D fluoroscopic overlay images can be rendered under a given C-arm view angle to provide 3D anatomical information as well as a graphical representation of the interventional plan that can be combined with the live x-ray fluoroscopy image.

Methods are known for utilizing a laser fixed to the C-arm and orientated along the planned path of a needle puncture to orient the actual needle along a desired puncture path so that it intersects a targeted location within the patent. Proper orientation of the laser can require manual adjustment of the patient table and/or a C-arm to ensure that the actual needle path coincides with the "virtual" (i.e., theoretical) laser path. This is because not all theoretical paths may be achievable with a C-arm, since the C-arm may be physically limited in angulation and also may be limited so that it does not collide with the patient or physician. The advantage of laser-based guidance methods, however, is that a biopsy needle can be oriented without exposing the patient or physician to x-ray radiation.

Other methods are known for positioning a needle along a virtual path without the use of a laser fixed to a specific position with respect to the C-arm. Such methods instead utilize x-ray radiation to orient the needle position. To adjust the C-arm so that a needle is correctly oriented along a desired path, the puncture target and the skin entry point—which together define a "path of puncture"—are imaged on top of each other on an x-ray detector to provide a "bull's eye view" that enables appropriate adjustment of the C-arm to achieve a desired puncture path.

There is a need for a system and method that combine the benefits of both types of procedures in a way that minimizes overall radiation exposure to patients and practitioners.

SUMMARY OF THE DISCLOSURE

A method is disclosed for planning a percutaneous procedure for use in a system comprising an imaging system having a movable arm, an x-ray source and an x-ray detector and a display and a system controller connected to and in communication with the imaging system and display, comprising: providing a three-dimensional image data set of a patient tissue region; obtaining an x-ray image of the patient tissue region using the x-ray source and the x-ray detector; co-registering the three-dimensional image data set to the x-ray image acquired using the imaging system; obtaining a planned instrument trajectory based on target point data representative of a target object within the patient tissue region and another point along the planned instrument trajectory, which may be a skin entry point data representative of a skin entry point; and aligning an instrument along the planned instrument trajectory using one of a plurality of instrument guidance procedures, the one of a plurality of instrument guidance procedures being selected on the basis of the planned instrument trajectory and a position of the movable arm; wherein the plurality of instrument guidance procedures comprises a laser-guided procedure, an x-ray guided procedure, and a procedure that replans the instrument trajectory.

A system is disclosed for planning a percutaneous procedure for use in a system comprising an imaging system having a movable arm, an x-ray source and an x-ray detector and a display and a system controller connected to and in communication with the imaging system and display. The system further comprises a machine-readable storage medium encoded with a computer program code such that, when the computer program code is executed by a processor, the processor performs a method comprising: providing a three-dimensional image data set of a patient tissue region; obtaining an x-ray image of the patient tissue region using the x-ray source and the x-ray detector; co-registering the three-dimensional image data set to the x-ray image acquired using the imaging system; obtaining a planned instrument trajectory based on target point data representative of a target object within the patient tissue region and a skin entry point data representative of a skin entry point; and aligning an instrument along the planned instrument trajectory using one of a plurality of instrument guidance procedures, the one of a plurality of instrument guidance procedures being selected on the basis of the planned instrument trajectory and a position of the movable arm; wherein the plurality of instrument guidance procedures comprises a laser-guided procedure, an x-ray guided procedure, and a procedure that replans the instrument trajectory.

BRIEF DESCRIPTION OF THE DRAWINGS

The accompanying drawings illustrate preferred embodiments of the disclosure so far devised for the practical application of the principles thereof, and in which.

DETAILED DESCRIPTION

Definitions

Figure 1:
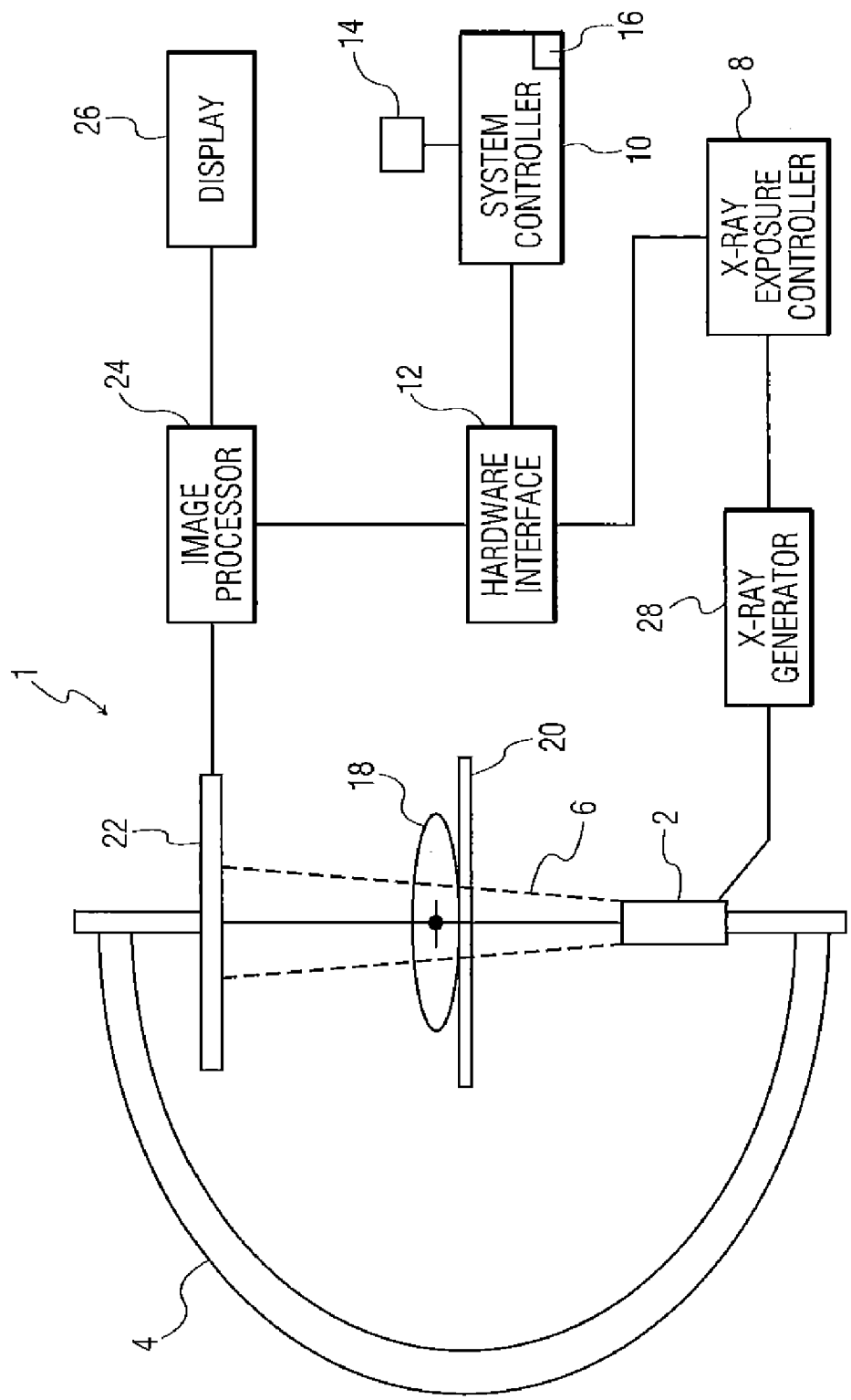
FIG. 1 is a is a schematic diagram showing an exemplary x-ray acquisition system for performing the disclosed method.

An "imaging system" is a system that includes at least a movable arm, an x-ray source, an x-ray detector, a display and a system controller. A "patient 3-dimensional image data set" is a three dimensional numerical array whose elements hold the values of specific physical properties at points in space inside the patient's body. A "multiplanar reformation image (MPR)" is a planar cross-section of the patient 3-dimensional image data set generated by cutting through the three-dimensional data set at some orientation (e.g., axial, coronal, sagittal, or oblique). A "fluoroscopic image" is a two-dimensional x-ray projection image showing internal tissues of a region of the body. A "live fluoroscopic image" is a sequence of x-ray images taken successively showing live movement of internal tissues of a region of the body. A "combined image" is an image in which an x-ray image is combined with a two-dimensional rendering of a three-dimensional data set computed under the same orientation as the x-ray image. A two-dimensional rendering of a three-dimensional data set is also referred to as a fluoroscopic overlay image or overlay image. "Co-registering" means aligning an x-ray image with a patient 3-dimensional image data set such that associated features within the x-ray image and a two-dimensional overlay image generated from the patient 3-dimensional image data set appear at the same location on a display in which the x-ray image and the overlay image are shown together. Co-registration can be point-based or gray-level based. In point-based co-registration, a transform is applied to the 3-dimensional image data set such that points in the resulting overlay image line up with their counterparts in the x-ray image as closely as possible. Gray-level based co-registration techniques determine the transform not by minimizing the distance between associated points in the overlay image and x-ray image, but by minimizing an error metric based on the resulting overlay image's gray levels and the x-ray image's gray levels. Co-registration can be static or elastic. In the latter case, the 3D data set may not only be rotated and shifted but warped as well. "Instrument" refers to any object which may pierce tissue of a patient, a non-limiting listing of which include needles and other biopsy devices, screws, implants, cannula, endoscopes, and anything else that can be inserted into a patient's body either percutaneously or intravascularly. A "skin entry point" is the position on a patient's skin at which an instrument is inserted. "Skin entry point data" is data representative of the skin entry point within the patient 3-dimensional image data set or within two x-ray views taken under different view orientations using a triangulation technique. A "target" or "target point" is a point within the body of a patient that is the subject of a percutaneous procedure. "Target point data" is data representative of the skin entry point within the patient 3-dimensional image data set or within two x-ray views taken under different view orientations using a triangulation technique. A "planned path" is a line generated between the skin entry point and the target point. "Instrument trajectory" is a desired trajectory of the instrument defined by the planned path. A "Bull's Eye View" is an x-ray view under which a target point and another point along the instrument trajectory are projected onto each other. The other point along the instrument trajectory may be the skin entry point. The movable arm view direction can be visualized using a graphical overlay in which the target point and skin entry point, forward-projected from 3-dimensions to 2-dimensions, are displayed as individual circles. If the Bull's Eye View has been reached, these two circles are projected at the same 2-dimensional position (i.e., they appear concentrically aligned). A "progression view" is an x-ray image taken at an oblique angle with respect to a line joining the skin entry point and the target. The term movable arm tomographic reconstruction refers to a technique in which multiple x-ray images taken along a particular image acquisition trajectory of the movable arm system, e.g., a partial circle. The multiple x-ray images are used to construct a patient 3-dimensional image data set. An "optical axis," or "central ray" is an imaginary straight line passing through the midpoint of an x-ray source and the iso-center of the imaging device. In an ideal system geometry, the optical axis is perpendicular to the x-ray detector, intersecting the detector at its midpoint.

Referring to FIG. 1, an exemplary system 1 is shown for performing a percutaneous procedure. The system 1 may comprise an x-ray tube or source 2 and associated support and filtering components. The x-ray source may be affixed to a support, such as a movable arm 4 to allow the x-ray source to be moved within a constrained region. In one embodiment, the movable arm 4 is a C-arm. The constrained region may be arcuate or otherwise three dimensional, depending on the nature of the support structure. A collimator may also be included, which defines the size and shape of x-ray beam 6 emerging from the source. An x-ray exposure controller 8 and system controller 10 may also be included. System controller 10 may be a personal computer or any known controller capable of receiving and transmitting control signals to/from the above-described x-ray system components via a hardware interface 12. System controller 10 may include a user input device 14, such as a trackball, mouse, joystick, and/or computer keyboard to provide for user input in carrying out various system functions, such as mode selection, linearity control, x-ray dose control, data storage, etc. The system controller 10 may include a processor 16 executing instructions for performing one or more steps of the disclosed method.

In the illustrated embodiment, a patient 18 is shown on patient-support table 20 such that an x-ray beam 6 generated by the x-ray source passes through him/her onto a detector 22. In one embodiment the detector 22 is a flat panel detector that acquires digital image frames directly, which are transferred to an image processor 24. A display/record device 26 records and/displays the processed image(s). The display/record device 26 may include a display for displaying the displayed image output, as well as a separate device for archiving. The image is arranged for storage in an archive such as a network storage device. The x-ray source 2 is controlled by the system controller 10 via exposure controller 8 and x-ray generator 28. The position of the x-ray source 2 may be adjusted via a drive system associated with the movable arm 4. The movable arm 4, x-ray source 2, x-ray detector 22, display 26 and system controller 10 may together be referred to as an imaging system.

As previously noted, laser-guided and radiation-guided systems are known for use in guiding instruments during percutaneous procedures. Although two specific laser guidance and x-ray guidance systems and methods will be described herein, it will be appreciated that the specifics of each system are not critical, and that any of a variety of other laser guidance and/or x-ray guidance systems and methods may be used with the disclosed system and method.

Workflow Steps

Figure 2:
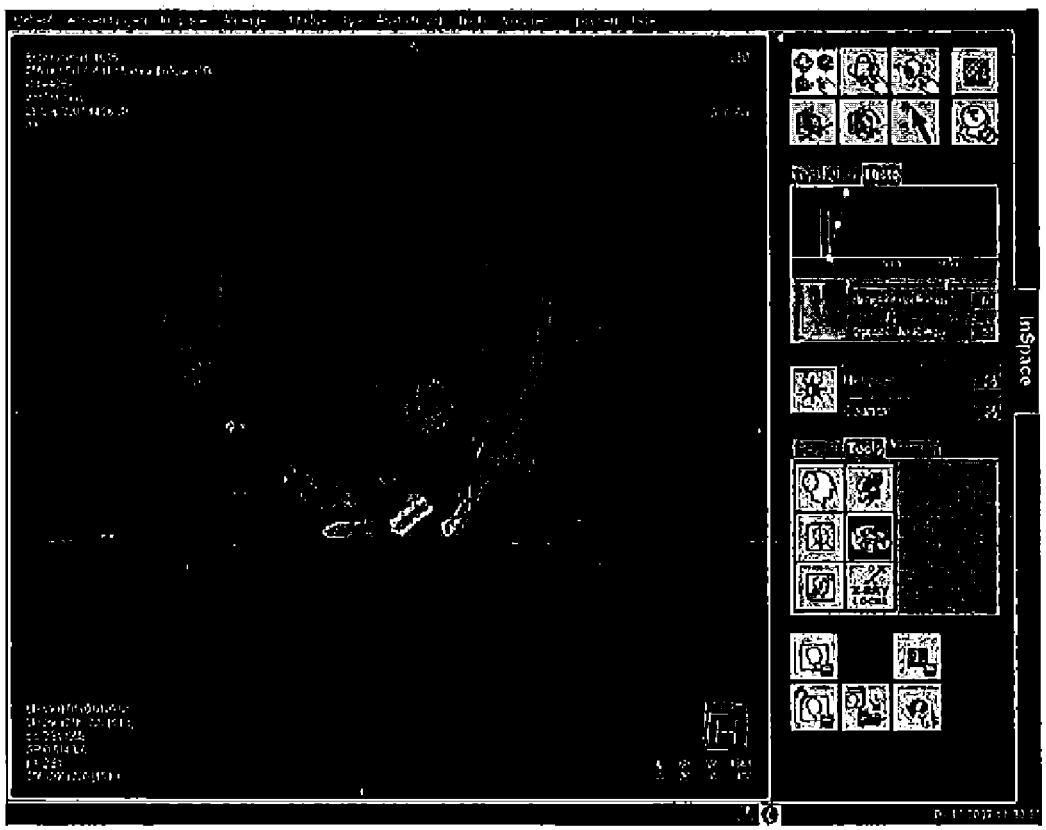
FIG. 2 is a display view from an x-ray guidance system showing a three-dimensional rendering of a test phantom showing objects internal to the phantom that are representative of different types of patient tissue.

Initially, a 3-dimensional data set of a targeted region within the patient will be obtained using one of a variety of techniques, such as computed tomography (CT), magnetic resonance imaging (MRI), positron emission tomography (PET), C-arm tomographic imaging (syngo DynaCT, Siemens A G, Forchheim, Germany) or the like. Referring to FIG. 2, a 3-dimensional rendering of such a 3-dimensional data set is shown. In the illustrated embodiment, the 3-dimensional dataset has been loaded into an appropriate 3D rendering program, such as the Siemens InSpace system, for viewing (the figures show 3-dimensional images representative of test phantoms that have a plurality of objects placed inside to simulate vessels, landmarks and targets).

The x-ray views (fluoroscopic images) obtained using the movable arm 4, source 2 and detector 22, need to be appropriately "registered" with the overlay images derived from the 3-dimensional data set for the region of interest of the patient. Data registration may be performed manually, automatically or semi-automatically (i.e., computer assisted). This registration step ensures that the fluoroscopic (x-ray) images of the patient obtained using the source 2 and detector 22 match the images of the patient constructed from the 3-dimensional data set. This enables instrument positioning using information on target position obtained from the 3-dimensional data set. In one embodiment, the co-registration step is performed by minimizing an error metric based on gray levels of a resulting overlay image and the x-ray image. In another embodiment, the co-registration step is performed by applying a transform to the 3-dimensional image data set such that points in a resulting overlay image align with counterpart points in the x-ray image.

Once the 3-dimensional data set has been appropriately registered to the 2-dimensional x-ray geometry, the instrument trajectory may be planned. To this end, the user may select a target point, Xt, and a skin entry point, Xe within the overlay images by visualizing the areas within a particular image and clicking on the point(s) using a selector such as a mouse button. Alternatively, the instrument trajectory may be planned before the registration step. In either case, registration ensures that the planned trajectory is mapped to the corresponding anatomical environment.

Figure 3:
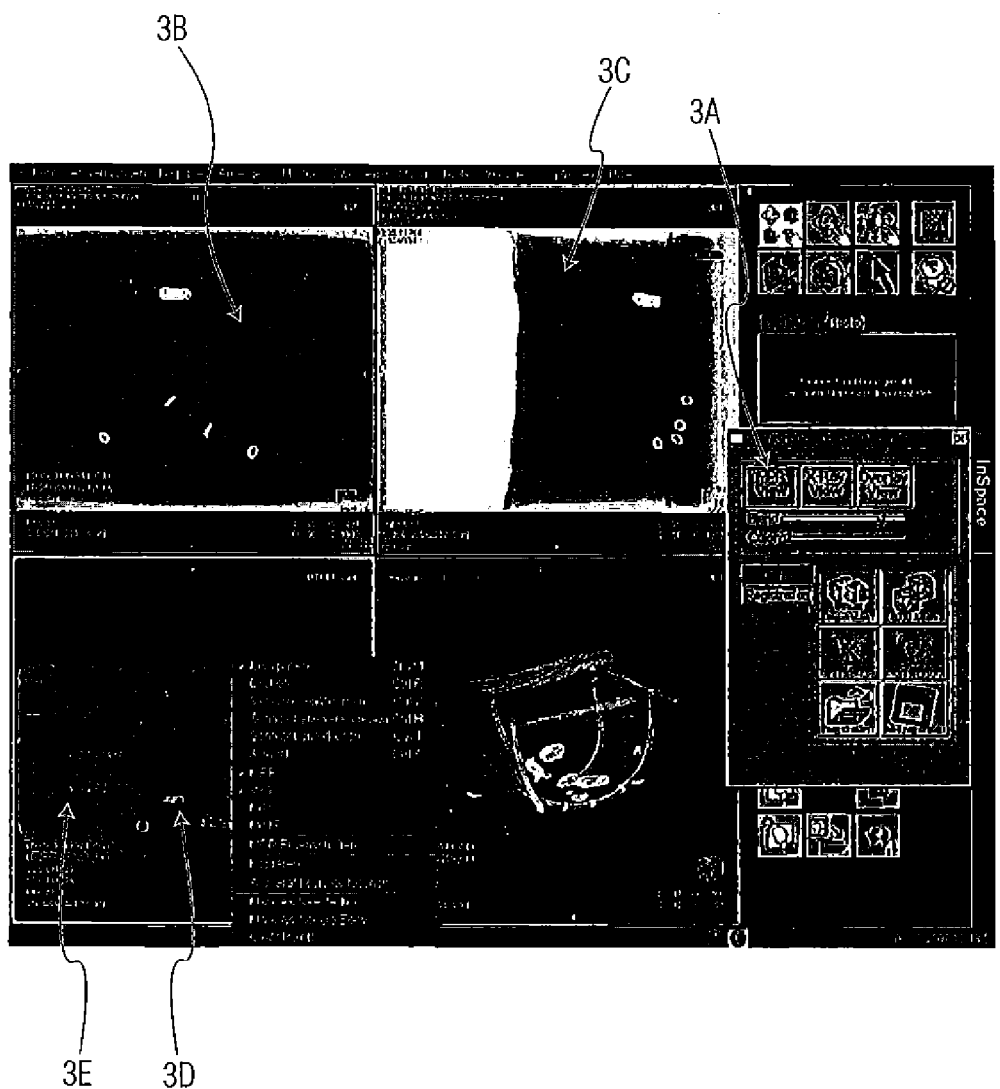
FIG. 3 is a display view showing the selection of a target point on the first and second fluoroscopic views and the MPR view.

As shown in FIG. 3, target point selection may be done by selecting a desired MPR view, such as by a right-click of a mouse pointer on an appropriate soft key 3A in a pop-up window in the display. In the illustrated embodiment, this results in desired MPR views being displayed in the upper left quadrant 3B, and upper right quadrant 3C. The target point is "selected" by clicking with a mouse pointer at the target position 3D in the lower left quadrant MPR display 3E. The skin entry point may be selected ("clicked") in the same manner.

Based on where the click points are made in the MPR view, the system obtains data representative of the target and skin entry points using data from the 3-dimensional patient data set. Using the target point data and skin entry point data, the system generates a graphical overlay showing a line which represents the planned instrument trajectory. Such a graphical overlay is applied to each of the images shown on the user display (as seen as line 4F in FIG. 4). This graphical overly may consist of the target and skin entry points, as well as a line intersecting the two, and may be overlaid onto one or more of the display views (e.g., x-ray, MPR, 3-dimensional rendering) as desired by the user. Since the x-ray views and the patient 3-dimensional image data set are registered with one another at this point in the procedure, the system can map the exact location of the target point Xt, and the skin entry point Xe (as well as the connecting vector "n") at their precise locations on each of the display views. As will be described in greater detail later, the displayed line represents the planned instrument trajectory.

Figure 4:
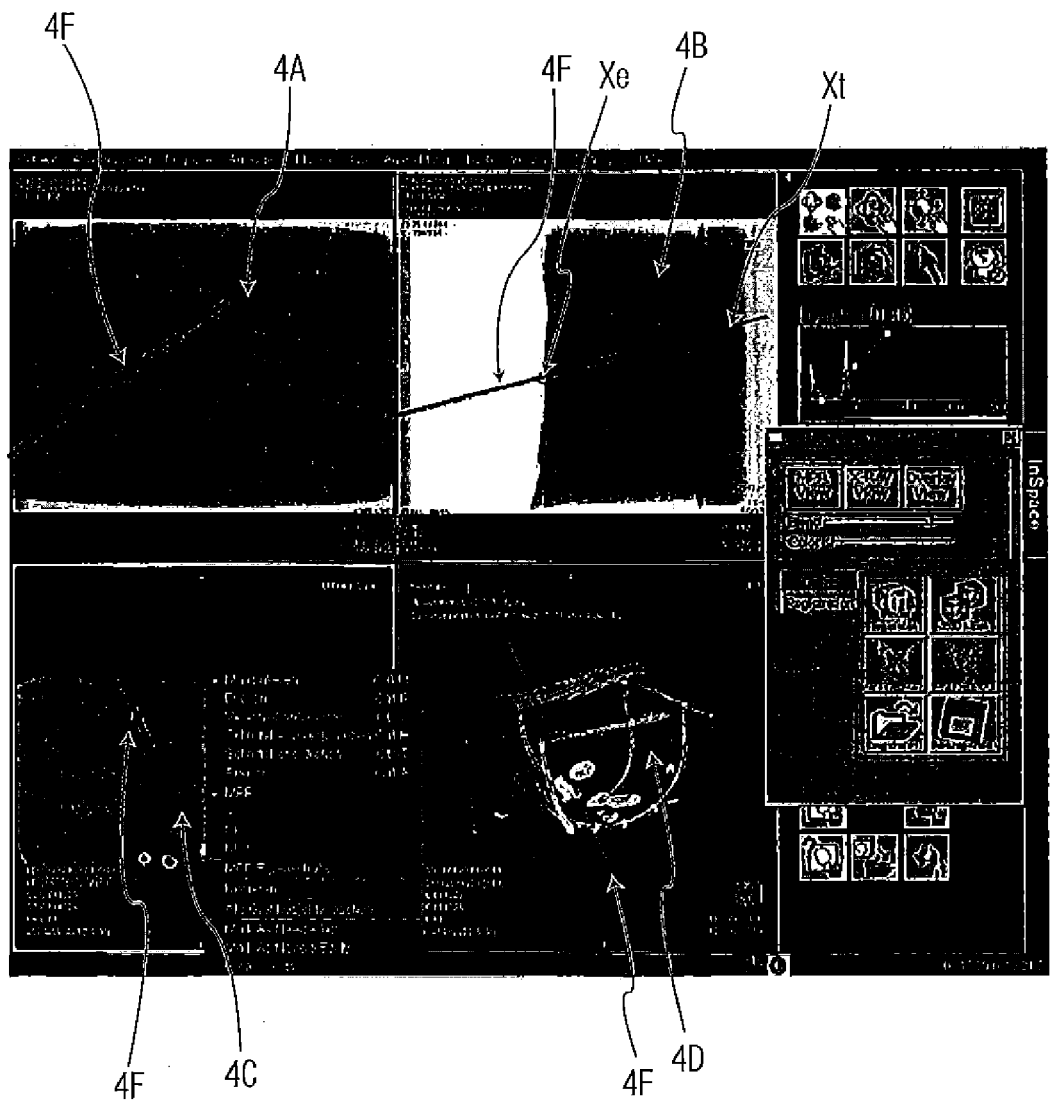
FIG. 4 is a display view showing the selection of a skin entry point on the first and second fluoroscopic views and the MPR view.

As shown in the four display quadrants 4A, 4B, 4C and 4D of FIG. 4, the skin entry point Xe and the target point Xt define a line 4F (shown in 4 places) in 3-dimensional space having a path vector (n=Xe−Xt). It will be appreciated that, as an alternative to defining the path vector using two points in space, the trajectory could instead be defined using xt and the path vector "n". This may be appropriate, for example, in the case where the patient is large and the skin entry point cannot be seen in the movable arm CT (i.e., it is outside the physical range of the movable arm CT). In such a case, the user may not need to see the exact location of the skin entry point if there are no organs in the immediate area (e.g., where there is only fat tissue). Whether this is indeed the case or not can be checked if the registered 3-dimensional patient data set comprises the complete volume of the patient or if there is another 3-dimensional data set (e.g., CT, MRI) that provides similar information in outer patient regions. In such a case, the physician may simply "click" the desired target point xt in the appropriate display view(s), and may "click" a second point that is visible in the movable arm CT to define a desired path vector n without specifying an actual skin entry point Xe. A desired instrument trajectory is a straight line (path vector) "n" that originates outside the patient's body and passes through the skin entry point xe and the target point xt without crossing bones or vital organs.

As shown in FIG. 4, the graphical overlay (i.e., the one in which points Xt and Xe are shown along with the line connecting them) may be combined with an anatomical image (i.e., an MPR view). In addition, the graphical overlay may be combined with both the forward projected anatomical image (overlay image) and live x-ray views. In the final movable arm position (again, the Bull's Eye View position), the graphical overlay may also adjust to different x-ray zoom conditions so that the user may confirm final positioning by revealing small deviations from the optimal view orientation. This resizing is automatically achieved through the use of a calculated conversion factor determined e.g., using a "similar triangles" technique.

Once the planned instrument trajectory is obtained, a determination is made regarding whether a laser guidance procedure can be performed, or whether an x-ray guidance procedure can be performed, or whether the path needs to be replanned. Laser guidance can be used if the planned instrument trajectory can be targeted in such a manner that the optical axis of the x-ray source on the C-arm coincides with the planned trajectory. Since the C-arm is calibrated to the 3D image data set, the system can automatically determine whether such an orientation is possible.

If the system determines that laser guidance cannot be employed, a determination is made regarding whether the C-arm can be made to coincide with the planned instrument trajectory so that the extension of the trajectory is projected onto the detector (is in the "Bull's Eye View"), in which case an x-ray guidance procedure can be used for instrument guidance.

If the planned instrument trajectory does not satisfy either of the aforementioned criteria, the instrument trajectory is replanned until at least an x-ray guidance procedure can be used. Of course, the user can re-plan the instrument trajectory more than once (e.g., if a laser-guided procedure is preferred, re-planning can be performed as many times as desired in order to achieve a planned instrument trajectory that meets the criteria for utilizing laser guidance).

Once a final instrument trajectory is obtained, the instrument is guided to the target using the selected guidance technique, as will be explained in greater detail below with reference to the respective procedure).

Exemplary Laser Guidance System and Method

Figure 5:
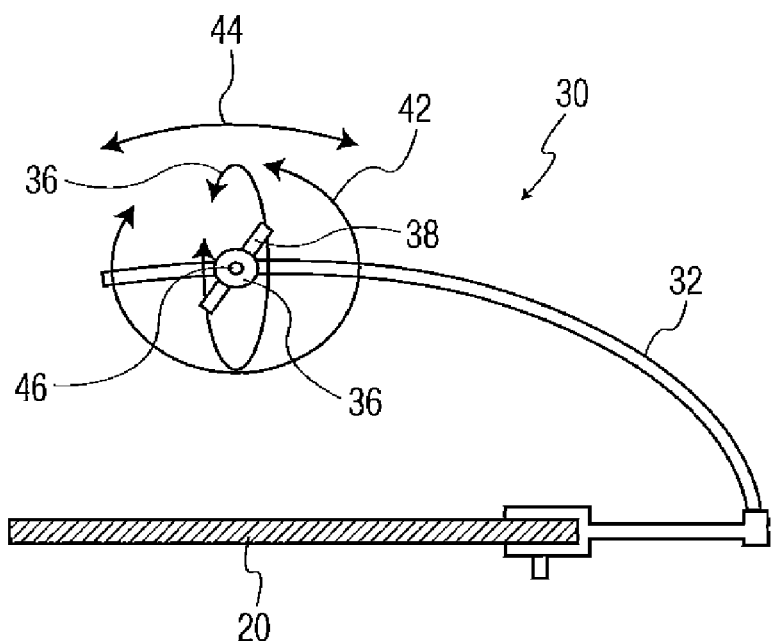
FIG. 5 is a side view of an exemplary arrangement for supporting a laser pointer for use with the disclosed methods.
Figure 6:
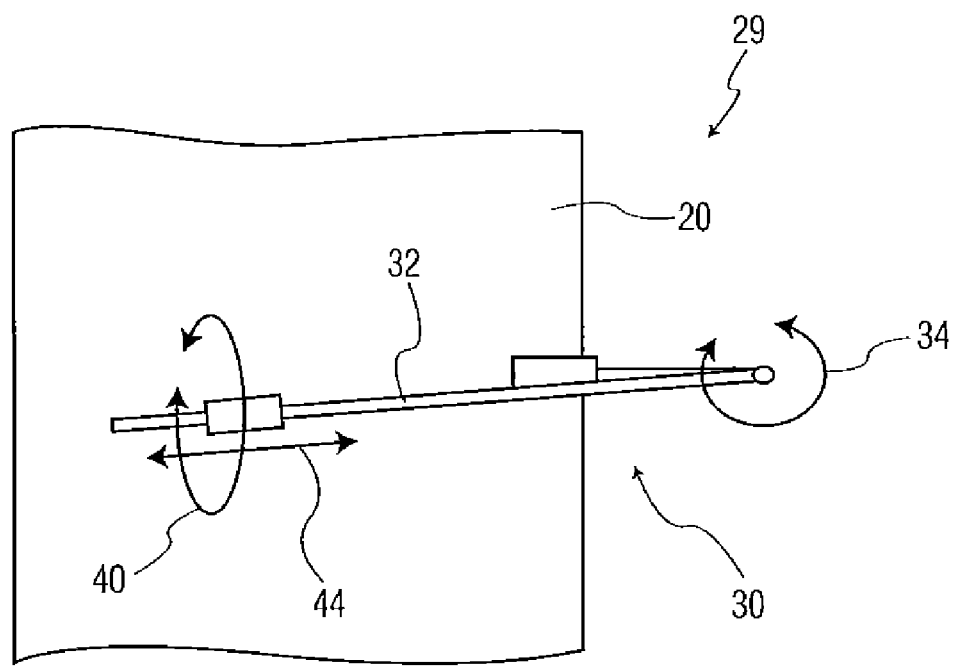
FIG. 6 is a top view of the arrangement of FIG. 5.

Referring now to FIGS. 5-10, an exemplary laser guidance system 29 for use with the disclosed method will be described in detail. Referring to FIGS. 5 and 6, a movable stand 30 is attached to a patient table 20. The stand 30 has a swivel arm 32 which is rotatable according to the arrow 34 in FIG. 6. A fastening device 36 is provided on the swivel arm 32, on which a laser pointer 38 is mounted. The fastening device 36 is designed in such a way that 3-dimensional movement of the laser pointer 38 is possible, in particular according to the motion arrows 40, 42 and 44.

The stand 32 may have a position sensor 46 through which the position of the laser pointer 38 is measurable relative to the patient table 20. The position sensor 46 may be used to define a coordinate system which can be recorded with the previously obtained 3-dimensional data set.

In one embodiment, motors may be used to achieve the automated movements according to the motion arrows 34, 40, 42 and 44. Such motors are not required, and the laser guidance system 29 can instead be moved by hand.

Figure 7:
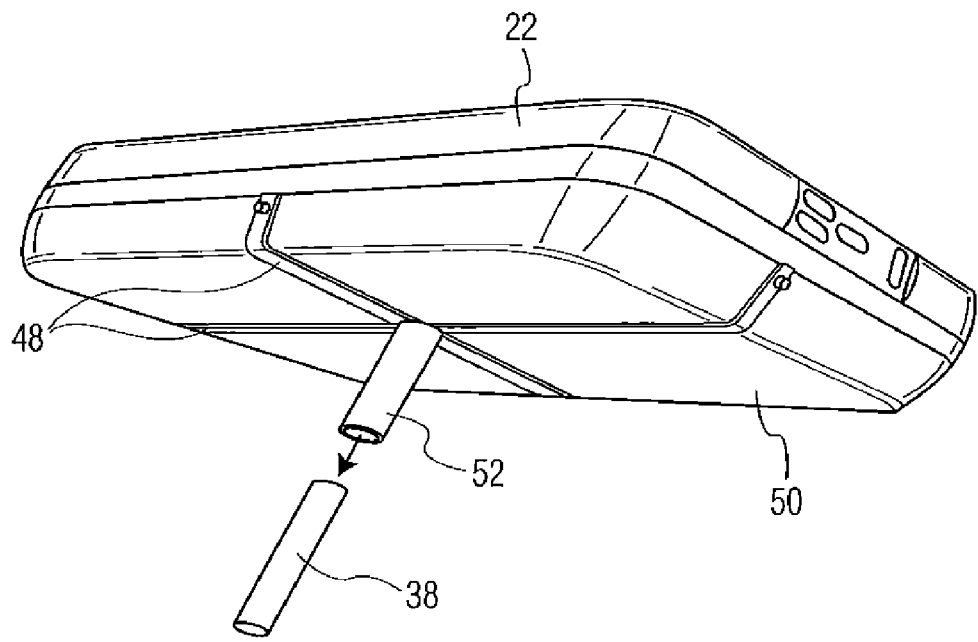
FIG. 7 is an isometric view of a flat x-ray detector in combination with a laser pointer.

In an alternative embodiment, the laser pointer 38 may be affixed to the x-ray detector 22. FIG. 7 shows the x-ray detector 22 to which two braces 48 are attached, which run parallel to the surface 50 of the x-ray detector 22. A sheath 52 is positioned perpendicular to the braces 48 and is used to attach the laser pointer 38. With this embodiment, to move the laser guidance system the entire x-ray detector 22 is moved, in particular the C-arm 4 is swiveled or tilted, to which the x-ray detector 22 and laser pointer 38 are attached.

In the event that no additional fluoroscopic images are deemed necessary during a percutaneous procedure, the laser pointer 38 can remain in the sheath 52. Where braces 48 are used to attach the laser pointer 38 to the x-ray detector 22, the braces and pointer may be separated from the x-ray detector 22 after reaching a desired instrument alignment.

Figure 8:
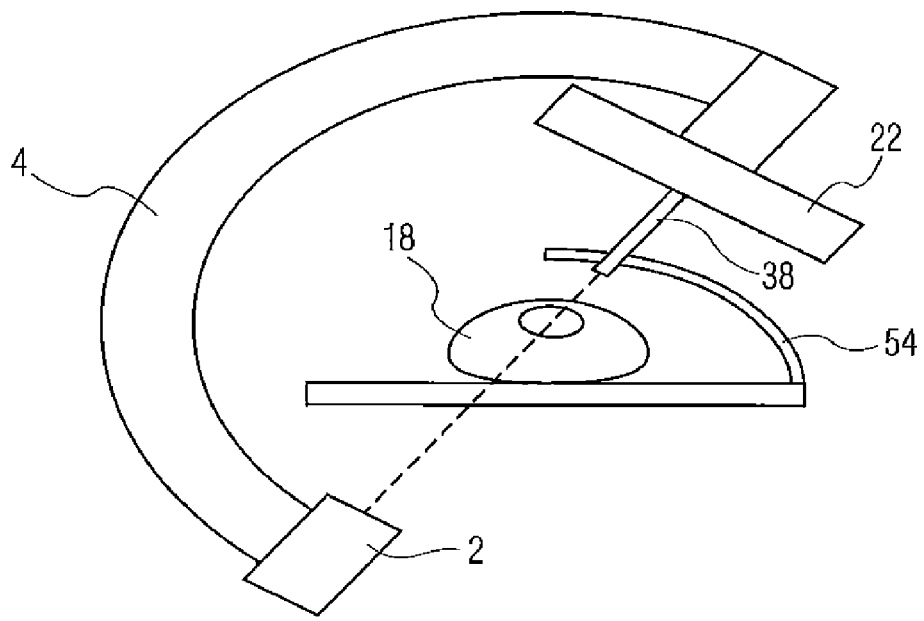
FIGS. 8 and 9 are schematic views of the interaction of the flat x-ray detector and laser pointer of FIG. 7 with the support arrangement of FIG. 6.
Figure 9:
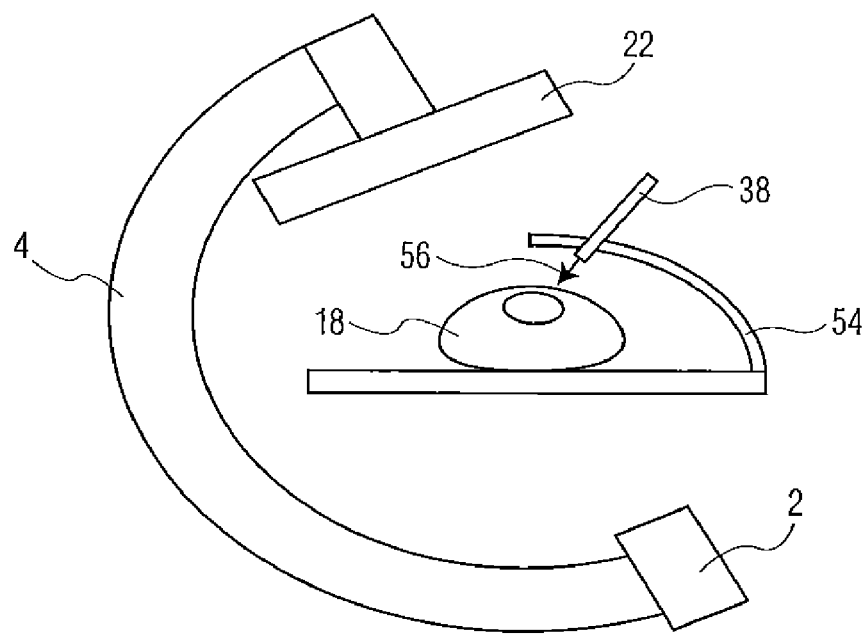

Referring now to FIG. 8, a stand 54, similar to stand 32 in FIGS. 5 and 6, may be used to guide the laser pointer 38. The laser pointer 38 may be fixed to the stand 54, separate from the x-ray detector 22. The C-arm 4 may be turned, e.g., into the position shown in FIG. 9. The laser pointer 38, since it is attached to the stand 54, remains aligned to the patient 18, and thus an instrument can be aligned along the laser beam 56 generated by the laser pointer 38. During the percutaneous procedure, fluoroscopic images can be taken using the x-ray source 2, x-ray detector 22, and C-arm 4 oriented at an oblique angle with respect to the instrument trajectory (as defined by the laser beam 56). As will be appreciated, these fluoroscopic images may aid the physician to guide the instrument precisely and accurately to the target.

Figure 10:
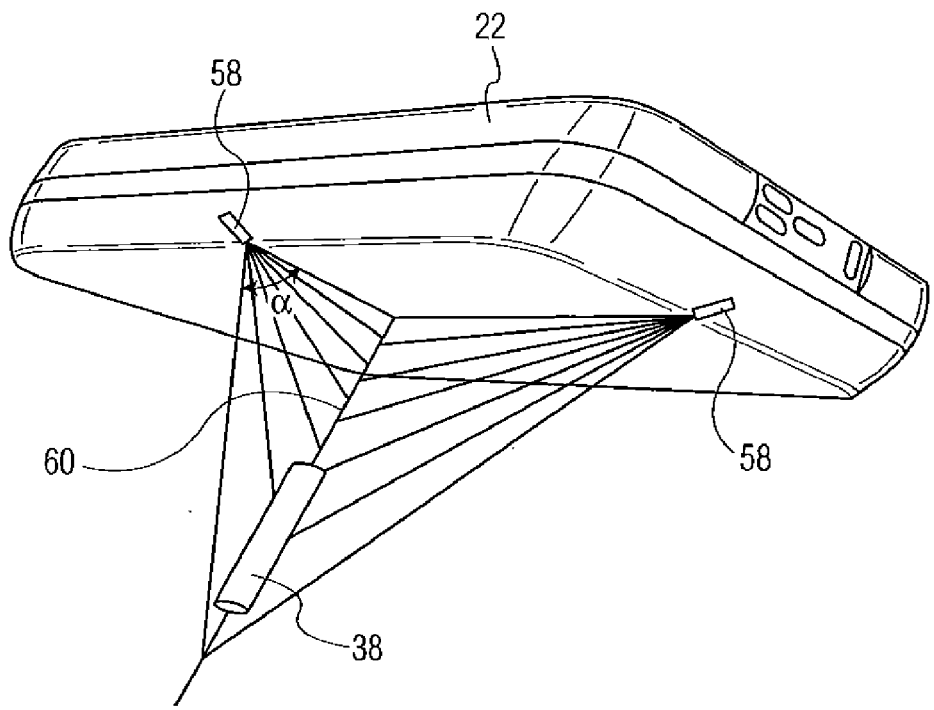
FIG. 10 is an isometric view of a flat x-ray detector in combination with a laser pointer according to another aspect of the disclosure.
Figure 11:
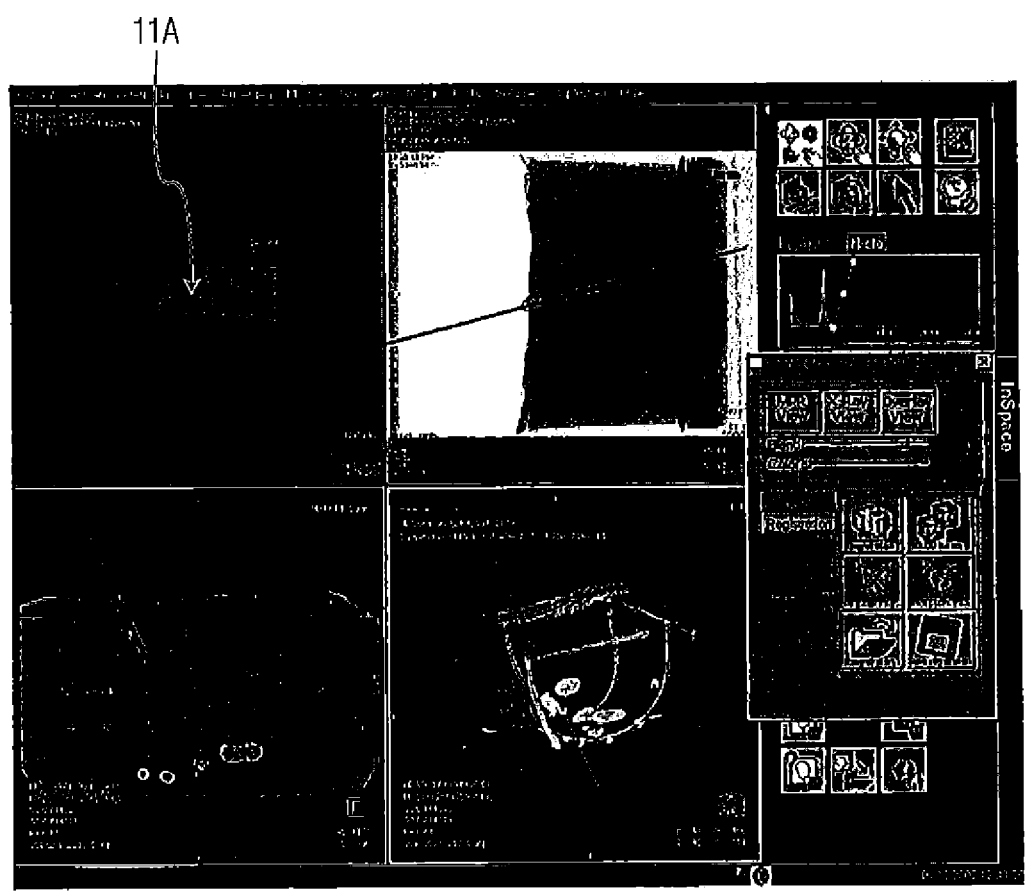
FIG. 11 is a display view from an x-ray guidance system showing a collimated fluoroscopic view of the target and skin entry points, as well as an oblique fluoroscopic view showing a planned path trajectory intersecting the target and skin entry points.

In a further alternative embodiment, a pair of laser sources 58 may be arranged on or near the edges of the x-ray detector 22 so that they are not visible in the images produced using the detector 22. Such an arrangement is shown in FIG. 10. The laser sources 58 may generate fan-shaped light in which a fan angle $\alpha$ is defined and along which the fan extends, such that produced laser beams are on a single level. The two levels intersect in a central straight beam line 60 such that this straight beam line 60 can readily be recognized by the user. The extension of the straight line 60 is the skin entry point Xe and the target point Xt, and thus represents the instrument trajectory. The instrument is aligned using this beam line 60. In one embodiment, a laser pointer 38 is aligned along straight beam line 60, and the x-ray detector 22 may be moved as desired to obtain one or more fluoroscope images, while the laser pointer 38 is used as part of the guidance system.

Exemplary X-ray Guidance System and Method

Referring now to FIGS. 11-17, an exemplary x-ray guidance system and method will be described in greater detail. As previously described, the system generates a line "n" between the skin entry point Xe and the target point Xt. This line is used to align the movable arm 4 to achieve a "Bull's Eye View," in which the two points are superimposed to show only a single point to the user. The instrument is placed at the skin entry point and aligned using the Bull's Eye View, shown in display quadrant 11A of FIG. 11, to orient the instrument along the planned instrument trajectory (i.e., one that hits both points). Initial alignment is verified using a fluoroscopic image of the oriented instrument. After the initial alignment is verified, the user inserts the instrument a short distance into the patient. One or more progression x-ray views are used to verify that the instrument is on the planned path between the skin entry point and the target point. The user may employ an iterative approach of inserting the instrument a small distance followed by a verification of the instrument's position using progression x-ray views to guide the instrument to the target. When the instrument reaches the target, a desired additional procedure may be performed, such as a biopsy, a drainage procedure, a radiofrequency ablation, or other medical interventional procedure.

Once an acceptable instrument trajectory has been planned, the movable arm 4 may be moved into the Bull's Eye View position. As previously noted, the Bull's Eye View orientation is one in which the skin entry point and the target point (Xe and Xt) overlie each other on the same detector positions (see FIG. 4). Adjustment of the movable arm 4 to achieve this positioning can either be performed manually or automatically.

In practice, positioning an instrument at the skin entry point Xe may be a difficult task, and thus a positioning aid may be used, such as a biopsy grid, a biopsy mesh, or other appropriate device. Once the appropriate instrument positioning has been achieved, collimation may be set around the Bull's Eye View to limit radiation exposure to the user and patient. Collimation may be either manual or automatic.

Figure 12:
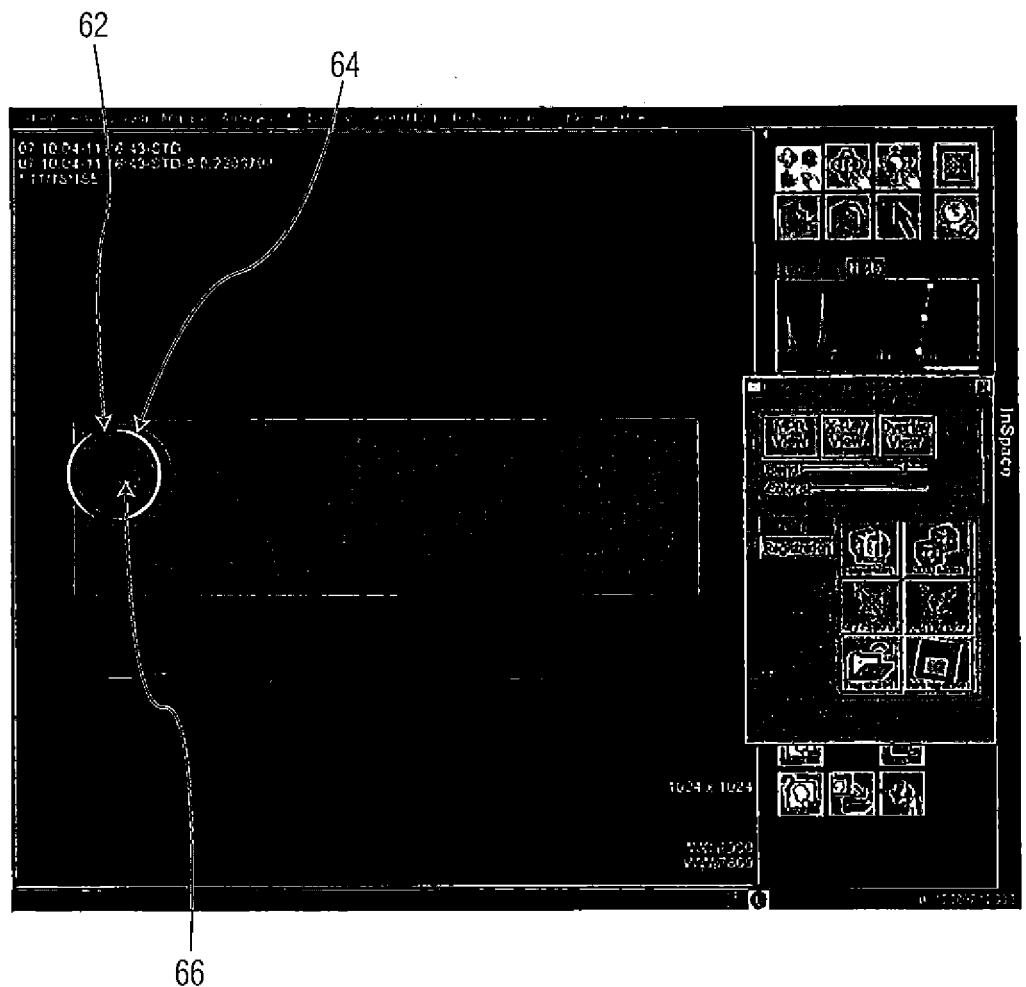
FIG. 12 is an enlarged view of the collimated fluoroscopic view of FIG. 11.

To facilitate fine adjustment of the instrument position, the Bull's Eye View may be isolated and enlarged, as shown in FIG. 12, to reveal slight deviations from the desired instrument positioning and orientation. Thus, FIG. 12 shows a switch from the four-quadrant view of FIG. 11 to a full-window view with an increased zoom level to reveal deviations from the ideal Bull's Eye View. As can be seen, the zoomed view of FIG. 12 shows concentric overlapping circles 62 (in black), 64 (in white) indicating that the Bull's Eye View has been achieved. In the illustrated embodiment, a SeeStar device (manufactured by Radi Medical Devices, Uppsala, Sweden) has been used to aid instrument positioning. The SeeStar device is an instrument guide that produces an elongated artifact in an x-ray image. This elongated artifact indicates the trajectory of an instrument inserted through the SeeStar, and thus it can be determined whether the selected trajectory will intersect the target as desired. The SeeStar shows up as a circle 66 (i.e., a black tube-like shadow in the figure) in the center of the displayed circles, which indicates that it is in the desired orientation (i.e., one that is in alignment with a trajectory that passes through the skin entry point and the target point). If the SeeStar were to show up as a line, its position/orientation would be adjusted, followed by re-verification of the new position/orientation by subsequent x-ray views.

As previously noted, in lieu of a SeeStar device, the user could instead use a hollow instrument guide to verify instrument placement. The hollow instrument guide may be configured so that it shows up as a point under fluoroscopy in the Bull's Eye View when a desired alignment is achieved. The hollow instrument guide may be clamped in position during fluoroscopy to limit radiation to the user, and its position may be adjusted and verified in a manner similar to that described in relation to the SeeStar device.

Figure 13:
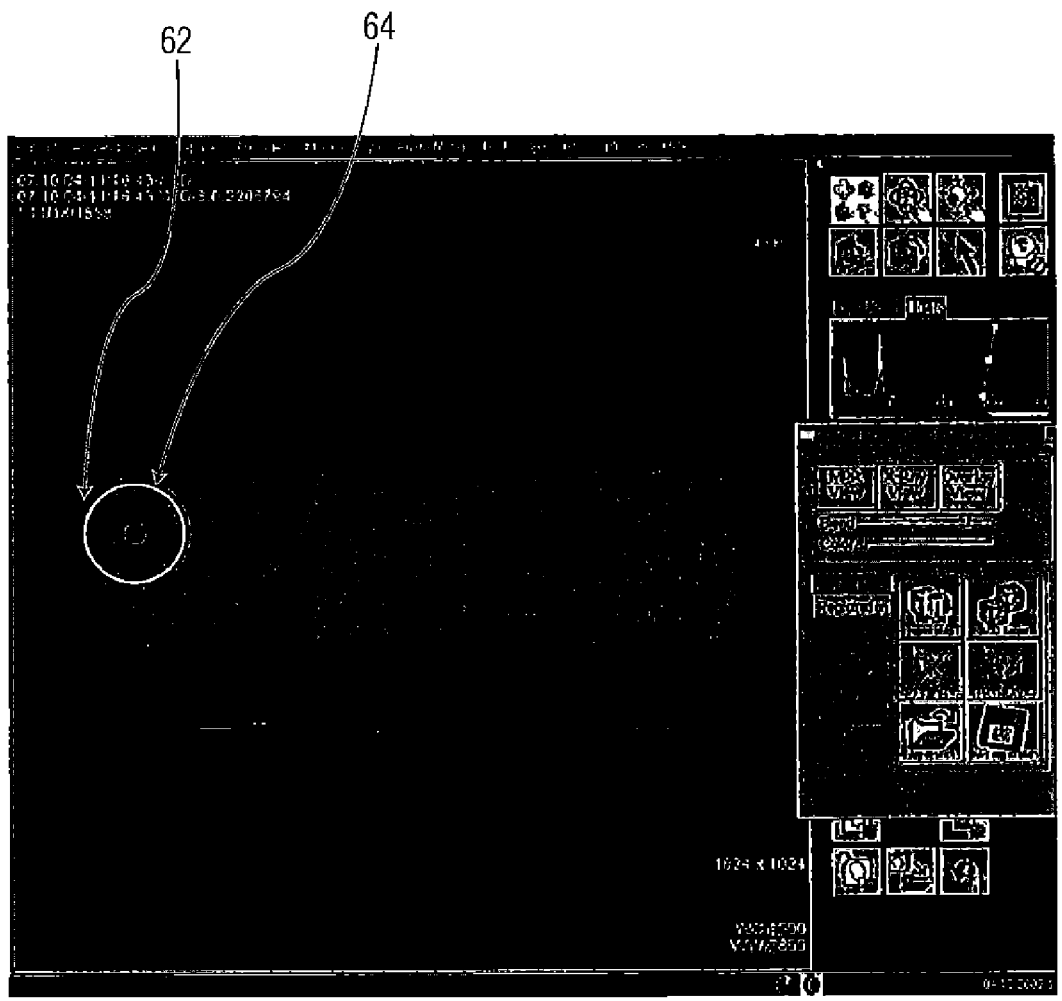
FIG. 13 is an enlarged view of the collimated fluoroscopic view of FIG. 11 showing an instrument inserted at the skin entry point.
Figure 14:
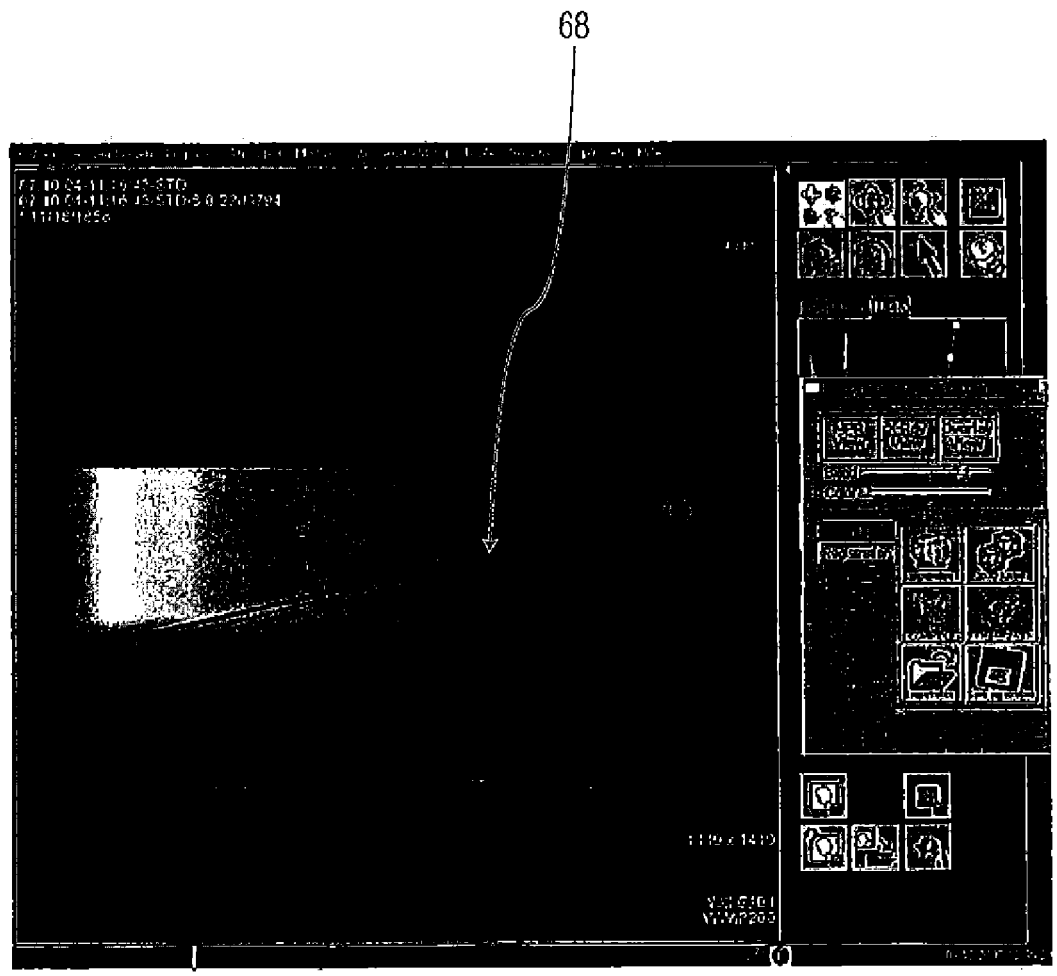
FIG. 14 is a collimated fluoroscopic view taken oblique to the view of FIG. 13 showing the position of the instrument relative to the graphical overlay of the planned instrument trajectory.

Once the desired instrument alignment is achieved, the instrument is pushed forward by a small amount into the patient tissue to stabilize the instrument's orientation. This insertion is performed under the Bull's Eye View. As shown in FIG. 13, the user can see straight down the instrument guide as well. The large circle represents the instrument body and instrument tip. In the illustrated embodiment they are exactly aligned, which is why only one large circle is visible in the figure. The black "bulb" in the center is the instrument (in the illustrated case, a needle). It appears in this way because it is almost (but not perfectly) aligned with the viewing direction. If the instrument were perfectly aligned, it would be shown as a circle in this view.

Instrument alignment may again be verified at this early stage of insertion. Such verification can be performed using x-ray "progression views," which are oblique x-ray views (i.e., non-Bull's Eye Views) obtained using the source 2 and detector 22. It will be appreciated that the user may also return to the Bull's Eye View at any time during the procedure to obtain additional information regarding instrument alignment. If a bi-plane x-ray device is available with the B-plane providing a progression, it is possible to check if the instrument remains aligned with the associated graphical overlay (shown as line 68 in FIG. 14) while the instrument is being pushed forward into the tissue. In the illustrated embodiment, the instrument appears as a thin diagonal line starting from the bottom left of the image, just above the graphical overlay line 68.

During the procedure, the movable arm 4 may be moved between the first and second progression views to enable the user to control the actual instrument movement from two oblique angles until the instrument has reached the target. When the target has been almost reached in one progression view, the user can return to the other progression view to confirm that the instrument has indeed been placed correctly before making the final push or releasing a spring-loaded biopsy device if one is used. The user can also return to the Bull's Eye View to obtain additional orientation information.

Figure 15:
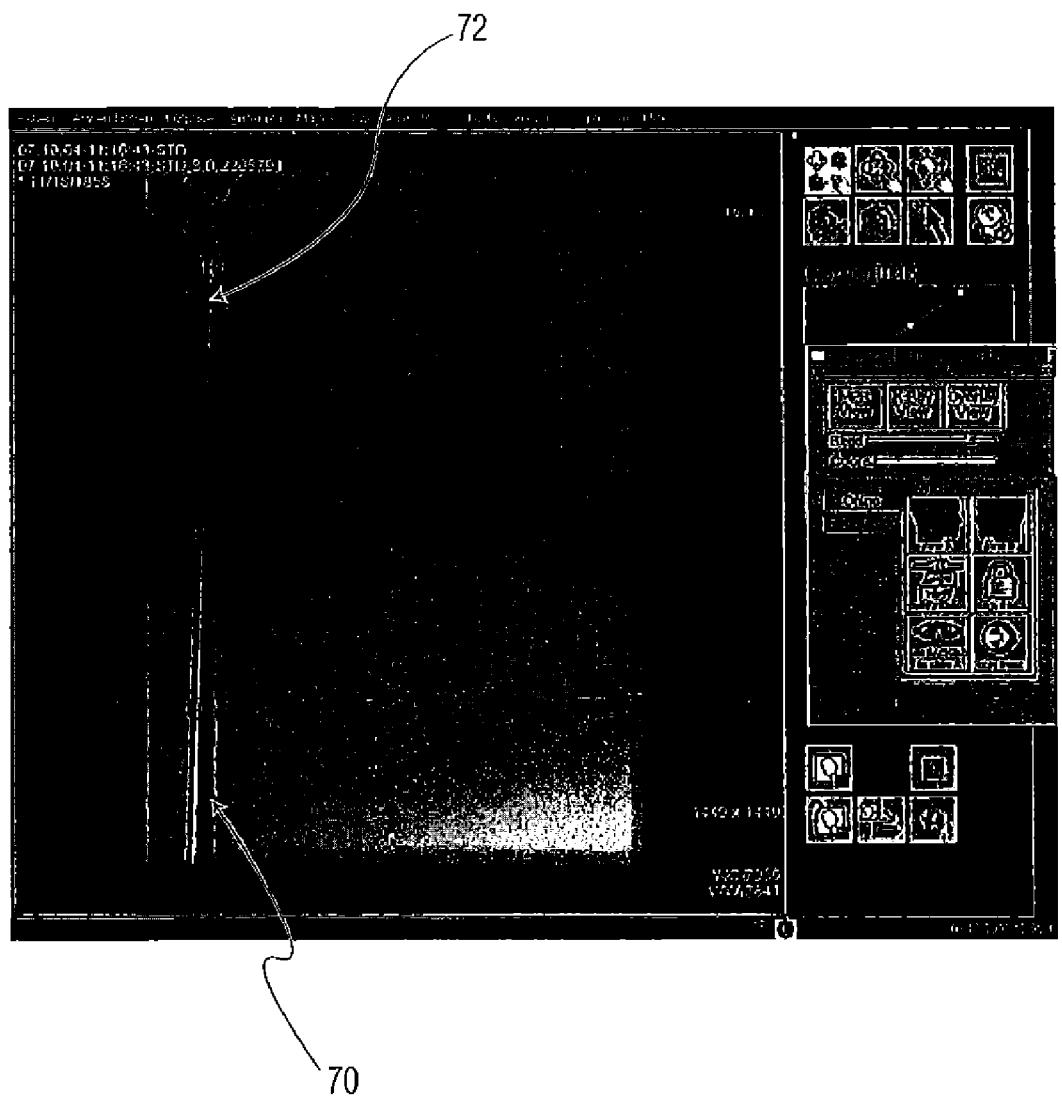
FIG. 15 is a collimated fluoroscopic view taken oblique to the views of FIGS. 13 and 14 showing the position of the instrument relative to the graphical overlay of the planned instrument trajectory.

Referring to FIG. 15, the movable arm is moved into the second progression view to check on instrument placement. If instrument 70 and graphical trajectory 72 align, the instrument 70 can be moved into the target. In the illustrated embodiment, a small degree of bend is shown in the instrument 70, which can occur when the instrument is small/thin and the target is dense.

Figure 16:
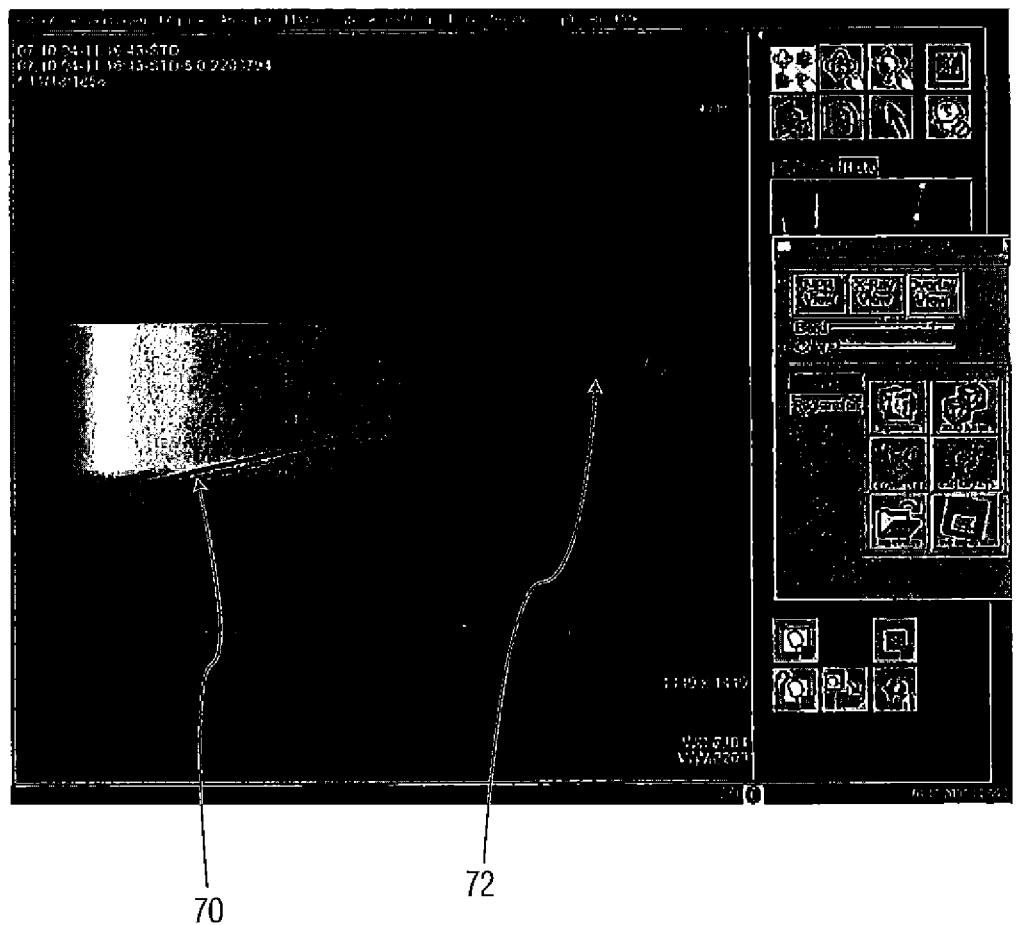
FIG. 16 is a collimated fluoroscopic view showing the position of the instrument as it intersects the target.

Referring to FIG. 16, a return to the first progression view is performed to confirm instrument placement at the target. It will be appreciated that if a bi-plane fluoroscopic device is available, there is no need to rotate the movable arm's A-plane back and forth between two progression views. Instead, the A-plane can be put at the first progression view while the B-plane is positioned under the second progression view, and both may be viewed simultaneously As an alternative to the use of progression views to verify instrument positioning during insertion, movable arm CT (DynaCT) acquisitions can be performed throughout the workflow to verify the instrument position and orientation at each stage of insertion. Such a movable arm CT acquisition can be performed at one or more stages of the procedure, as desired by the user. It is noted, however, that the movable arm CT procedure can take up to several minutes and increases the overall amount of radiation exposure to the patient. Progression views, by contrast, are relatively fast (almost instantaneous). The user simply rotates the movable arm (if required) to the desired progression view location, and releases the x-rays. The x-ray image shows up on the display in a few seconds.

Figure 17:
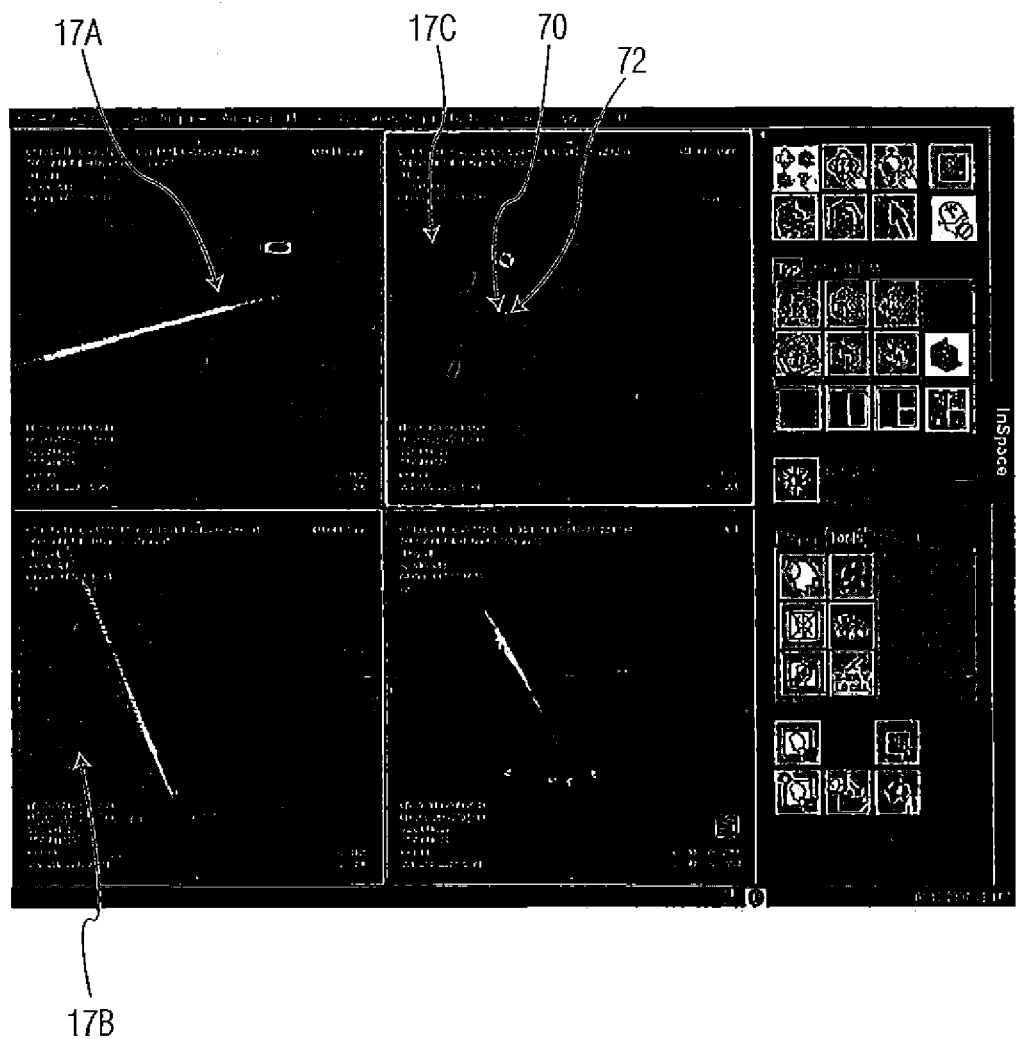
FIG. 17 is a C-arm CT (DynaCT) scan of the completed instrument insertion.

FIG. 17 shows a movable arm CT (DynaCT) scan of the completed instrument insertion position. Although not required, performing such a verification ensures that the positioning is correct prior to completing the procedure. As can be seen in the MPR views shown in the upper and lower left quadrants 17A, 17B of FIG. 17, the instrument 70 has been appropriately engaged with the target 72. The upper right quadrant view (which shows the Bull's Eye View), however, reveals that the instrument 70 just made it into the target 72.

Referring now to FIGS. 18A-18E, the disclosed method for selecting a guidance technique for performing a percutaneous procedure will be described in greater detail. At step 1800 (FIG. 18A), a patient 18 is placed on a table 20 in proximity to an imaging system having a movable arm 4, an x-ray source 2, an x-ray detector 22, a system controller 10 and a display 26. At step 1810, a 3D patient image data set of a patient tissue region is provided. At step 1820, an x-ray image of a targeted patient tissue region is acquired using the x-ray source and x-ray detector. In one embodiment (see FIG. 18B), at step 1822 obtaining an x-ray image of the patient tissue region using the x-ray source 2 and x-ray detector 22 comprises obtaining a plurality of x-ray images, displaying the plurality of x-ray images on the display 26 along with a three-dimensional rendering of the three-dimensional image data set, and an overlay image representing a 2-dimensional rendering of the 3-dimensional image data set. At step 1824, the skin entry point, the target point and the planned instrument trajectory are graphically displayed in their respective positions on the plurality of displayed x-ray images, the three-dimensional rendering and the overlay image. At step 1830 (FIG. 18A), the 3D patient data set is co-registered to the x-ray image acquired using the imaging system. In one embodiment (see FIG. 18C), at step 1832 the co-registering step comprises applying a transform to the 3D patient image data set such that points in a resulting overlay image align with counterpart points in the x-ray image. At step 1840 (FIG. 18A), the user plans an instrument trajectory in the 3D volume by selecting target point data representative of a target point within the patient tissue region, and skin entry point data representative of a skin entry point. The target point data and skin entry point data may be obtained from the co-registered 3D image data set. As a result of co-registration, it may also be possible to plan the instrument path immediately after step 1800. This may be beneficial if planning is performed on a pre-procedural data set acquired on an imaging device that is different from the C-arm imaging system.

At step 1850 instrument alignment is performed using one of a plurality of instrument guidance procedures, where the instrument guidance procedure is selected on the basis of the planned instrument trajectory, and a position of the movable arm 4. The plurality of instrument guidance procedures may include a laser guided procedure, an x-ray guided procedure, or a procedure that replans the instrument trajectory. If the planned instrument trajectory can be targeted in such a manner that the optical axis (central ray) of the x-ray source 2 on the C-arm 4 coincides with the trajectory, at step 1860 a laser guidance procedure (such as the one described previously in relation to FIGS. 5-10, and discussed in more detail below) is selected for instrument guidance. This determination is based on information relating to calibration of the C-arm with the 3D volume and a collision control feature of the system. The step of aligning the instrument may comprise aligning the instrument along a laser beam path generated by a laser pointer, the laser beam path intersecting the skin entry point Xe and the target point Xt (step 1852, FIG. 18D). At step 1854, the laser beam path may comprise the intersection of at least two laser fan patterns.

If the central ray of the x-ray source does not coincide with the planned instrument trajectory, and an extension of the planned instrument trajectory intersects with the x-ray detector 22, at step 1870 an x-ray guidance procedure (such as the one described previously in relation to FIGS. 11-17, and discussed in more detail below) is selected for instrument guidance. If a central ray of the x-ray source does not coincide with the planned instrument trajectory, and an extension of the planned instrument trajectory does not intersect with the x-ray detector 22, the instrument trajectory is replanned at step 1840. This replanning step may involve repositioning the patient by moving the patient table. At step 1890, a warning signal may be provided to the user if the central ray of the x-ray source does not coincide with the planned instrument trajectory, and an extension of the planned instrument trajectory does not intersect with the x-ray detector 22.

Figure 19:
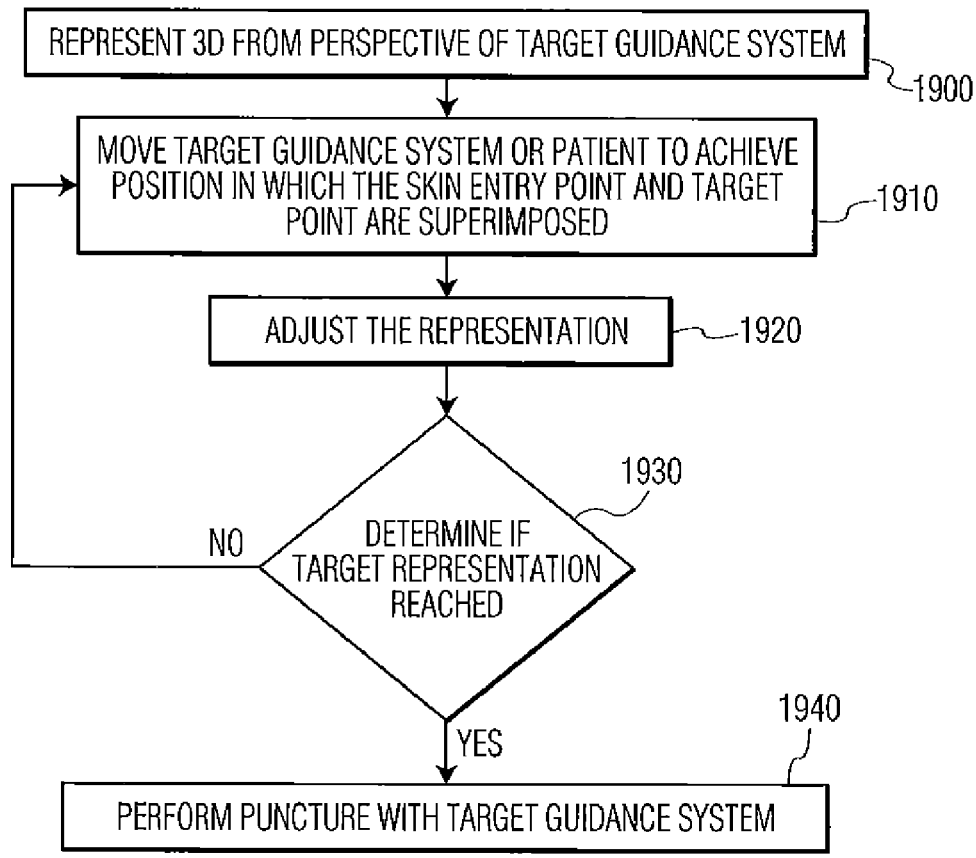
FIG. 19 is a flow chart showing a sequence of steps of a method for aligning an instrument using laser guidance.

If laser guidance can be employed, at step 1900 (see FIG. 19), the 3D image data set is represented from the perspective of the target guidance system. The target guidance system defines a vector in a view direction to the patient. The patient is assigned to the 3D image data set so that the target guidance system defines a view direction on the 3D image data set. This may occur so that the target guidance system is represented in the central point of the monitor as an X, and the target point should also be represented as an X. The skin entry point Xe and target point Xt may also be represented. The goal is for the target guidance system to precisely show these points superimposed on each other. It will be appreciated that the target may be represented as an X, while the skin entry point may be represented using a circle, or that circles may be used to represent both the target and skin entry points. Either graphical representation can be combined with a fluoroscopic overlay image representing the patient's anatomical structures.

The user may move the laser guidance system 29 or the patient 18 at step 1910 to achieve an appropriate position so that the points are superimposed. Because this movement changes the view of the laser guidance system to the patient and with it the 3D image data set, the representation is adjusted at step 1920. At step 1930, a check is performed to determine whether the target representation has been reached (i.e., whether all of the points align with each other). If the target representation is not achieved, steps 1910, 1920 and 1930 are repeated until the points are superimposed. Once the desired target representation is reached, at step 1940 the instrument is guided using the target guidance system. If the laser beam exactly aligns with the central x-ray of the x-ray source, the laser may be used by itself to provide instrument guidance. It will be appreciated that for instances in which the laser alone is used for instrument guidance, that the practitioner still may verify the instrument position within the patient using x-ray imaging.

In one embodiment, automatic positioning of the patient table 20 may be achieved at step 1910. The goal is to align the central x-ray of the x-ray source with the planned instrument trajectory. Thus, the position of the patient table 20 is automatically adjusted using positioning motors system until the planned instrument trajectory intersects the iso-center of the C-arm 4. The C-arm 4 is rotated such that its view orientation matches the orientation of the instrument trajectory.

Referring again to FIG. 18A, if, at step 1850 it is determined that laser guidance cannot be employed, but the planned instrument trajectory still can be targeted in such a manner that a central ray of the x-ray source can be made to coincide with the planned instrument trajectory so that the extension of the trajectory intersects with the detector 22 (the "Bull's Eye View"), at step 1860 an x-ray guidance procedure (such as the one described in relation to FIGS. 11-17) is selected for instrument guidance.

Figure 20:
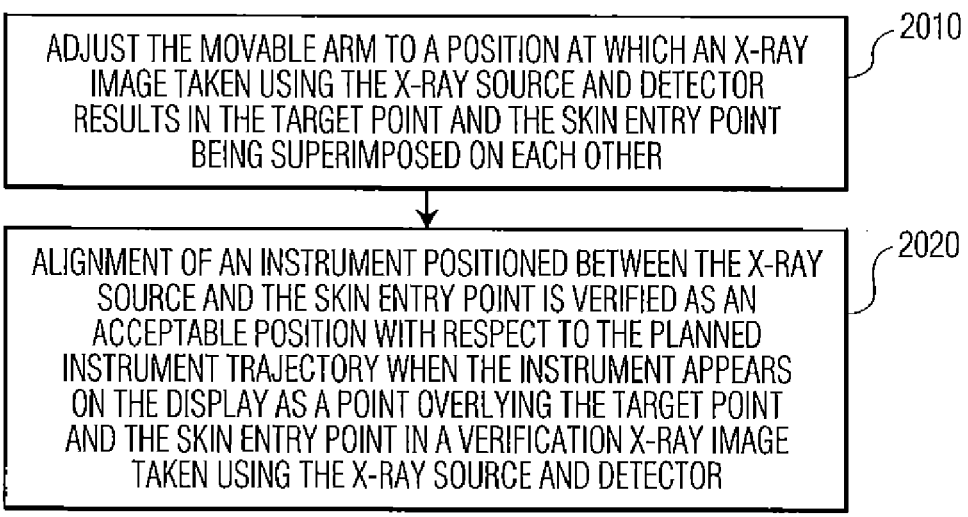
FIG. 20 is a flow chart describing a sequence of steps of an exemplary x-ray alignment method.

If x-ray guidance is used, at step 2010 (see FIG. 20), the movable arm 4 is adjusted to a position at which an x-ray image taken using the x-ray source 2 and the x-ray detector 6 results in the target point Xt and the skin entry point Xe being superimposed on top of each other. In one embodiment, the step of adjusting the movable arm may comprise determining a spatial orientation within the three-dimensional image data set at which the target point and skin entry point are superimposed on each other, and automatically moving the movable arm so that a further x-ray image obtained using the x-ray source 2 and detector 22 images the target and skin entry points onto the same pixels of the x-ray detector.

At step 2020, alignment of an instrument positioned between the x-ray source 2 and the skin entry point Xe is verified as an acceptable position with respect to the planned instrument trajectory when the instrument appears on the display as a point overlying the target point Xt and the skin entry point in a verification x-ray image taken using the x-ray source 2 and detector 22. In one embodiment, acceptable position with respect to the planned instrument trajectory is verified by taking multiple x-ray images using the x-ray source 2 and detector 22 at movable arm positions oblique to the position of the movable arm 4 used to obtain the verification x-ray image.

In further steps, the user may insert the instrument into the patient at the skin entry point. One or more progression x-ray views may be taken to ensure that the instrument remains aligned with the projected instrument path. It will be appreciated that the user may also return to the Bull's Eye View to gain additional insights regarding instrument orientation. The user may press the instrument further into the patient toward the target while making adjustments to ensure the instrument remains aligned with the projected instrument path. The pressing and progression x-ray steps may be repeated as desired by the user to guide the instrument in an incremental manner to intersect the target.

Referring again to FIG. 18A, if neither laser guidance nor x-ray guidance can be used (i.e., the central ray of the x-ray source does not coincide with the planned instrument trajectory and an extension of the planned instrument trajectory does not intersect with the x-ray detector, at step 1880 it is determined that the planned instrument trajectory needs to be replanned, and the process returns to step 1840 and the instrument trajectory is replanned. Replanning is performed that at least the instrument trajectory can be planned using a laser or x-ray guidance techniques, as determined again in steps 1850, 1860 and 1870. Where the system determines that the planned instrument trajectory cannot be targeted using either laser or x-ray guidance techniques (i.e., when a central ray of the x-ray source does not coincide with the planned instrument trajectory and an extension of the planned instrument trajectory does not intersect with the x-ray detector, an alert such as a warning or other signal may be provided to indicate to the user that the trajectory must be re-planned.

Figure 18A:
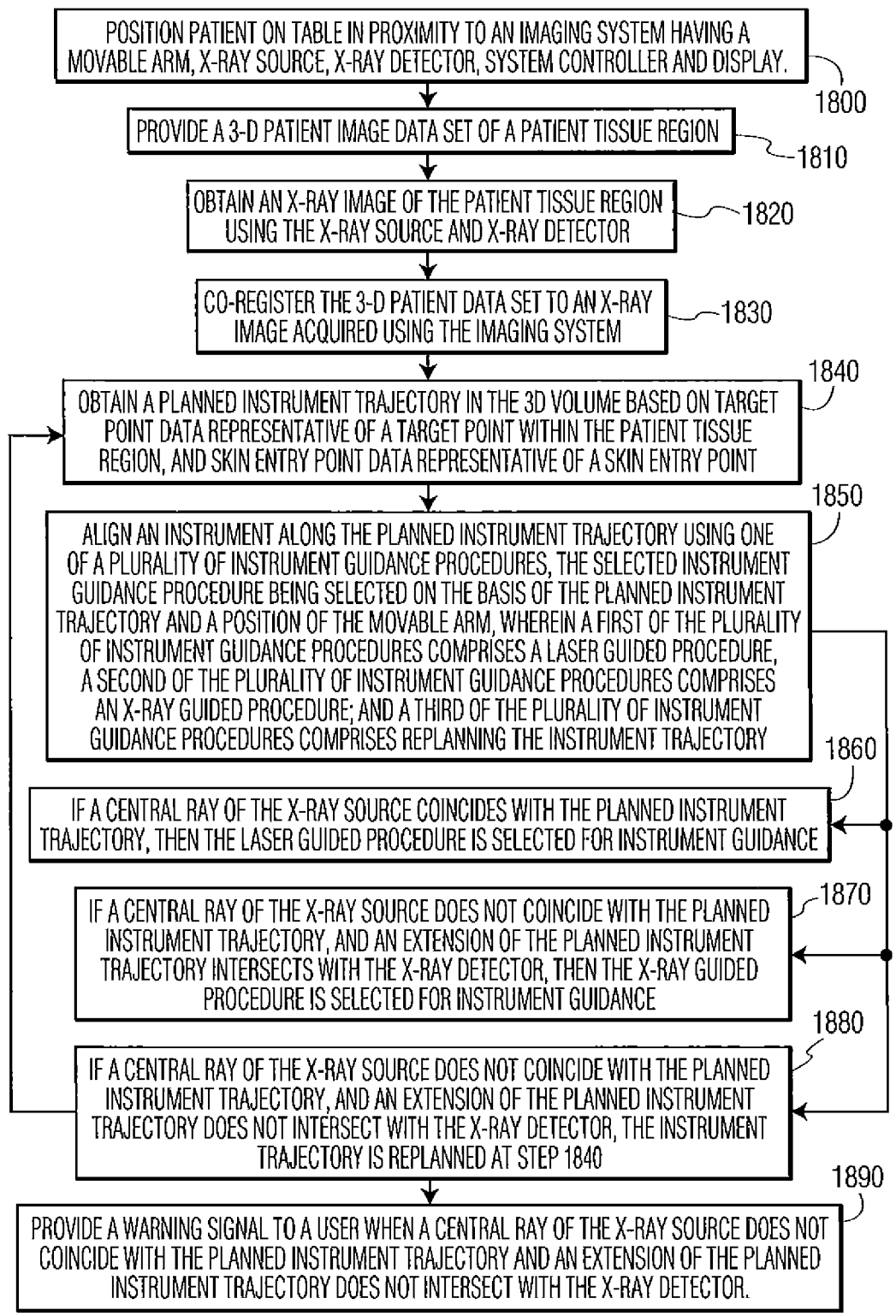
FIGS. 18A-18E are flowcharts for using the disclosed method to select between a laser guidance technique and an x-ray guidance technique for planning and performing a percutaneous procedure.
Figure 18B:
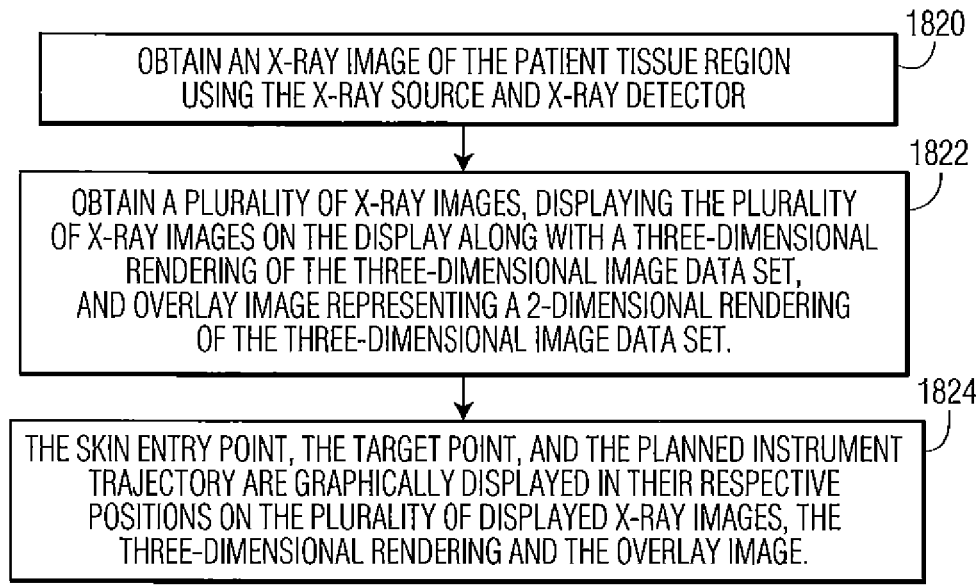
Figure 18C:
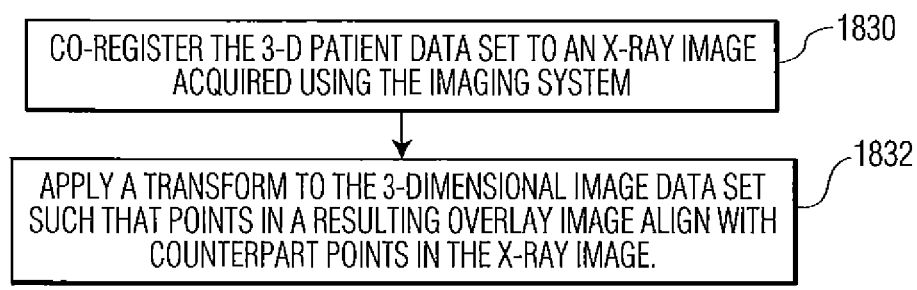
Figure 18D:
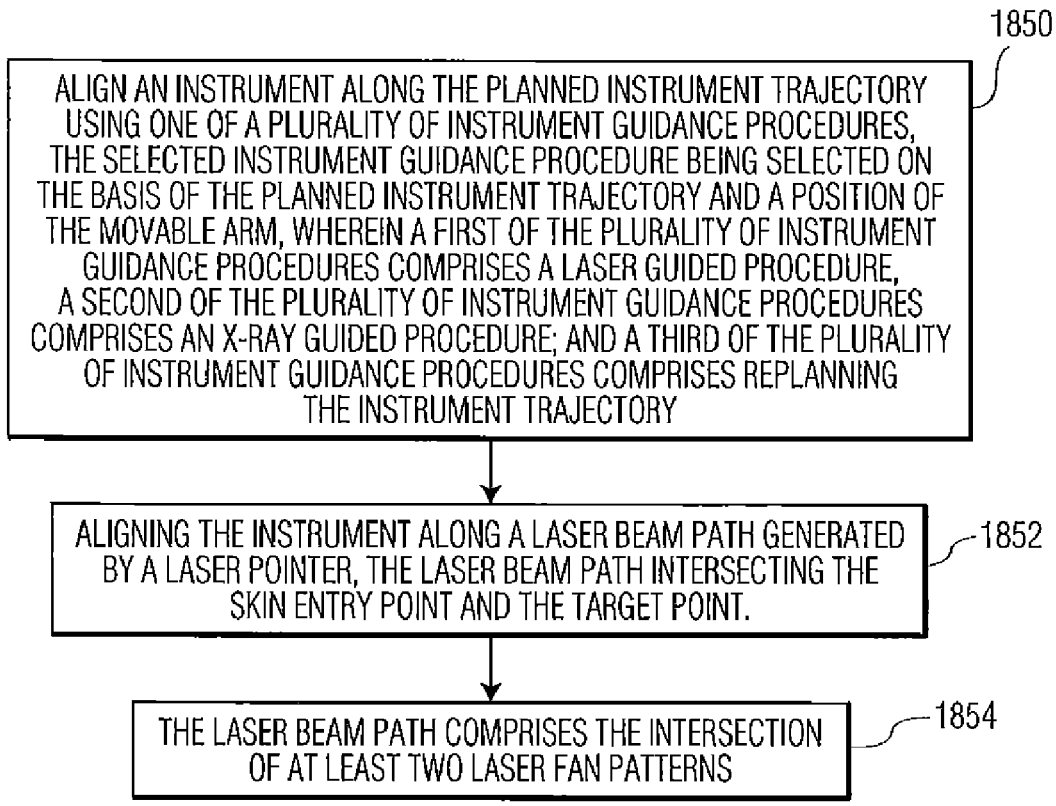
Figure 18E:
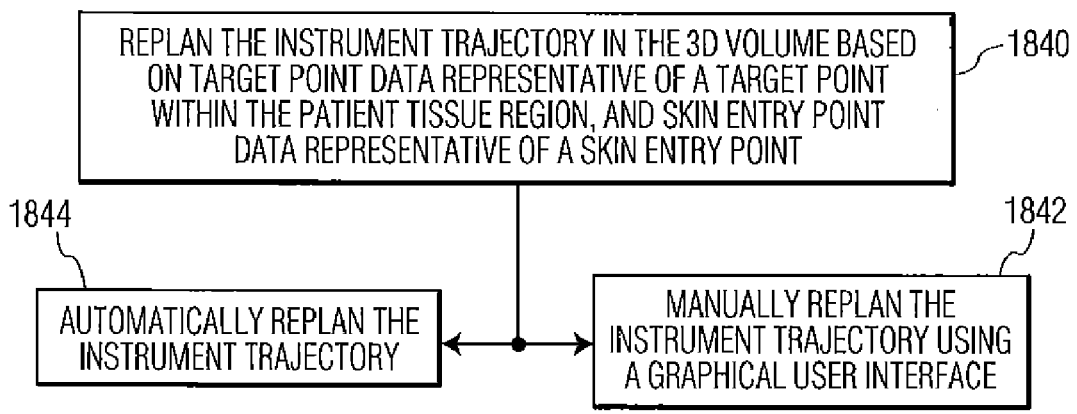

In one embodiment, shown in FIG. 18E, a suggested re-planned instrument trajectory may be automatically formulated and presented to a user so that either laser guidance or x-ray radiation guidance techniques can be used. Thus, at step 1842 re-planning may be carried out manually (using a graphical user interface (GUI)), or by means of a "tracked" instrument (as will be described in greater detail below). Alternatively, at step 1844 re-planning can be carried out automatically. Once the instrument is reoriented along the re-planned trajectory, the instrument may be advanced and controlled as described previously in relation to the laser-guidance and x-ray-guidance techniques.

In one alternative embodiment, skin entry point replanning may be facilitated by the use of an optical or electromagnetic position sensor attached to the instrument. The position sensor may automatically identify both the location and the direction of movement of the instrument so that when the position sensor is moved on the surface of the skin of a patient, the skin entry point Xe can be newly determined such that, given a stationary target point (but a variable "tracked" starting point), the resultant path of the instrument can automatically be entered into the 3D dataset (and rendered as desired). Once an appropriate instrument trajectory has been selected, the skin entry point Xe is automatically determined and a marking (e.g., color mark, optionally combined with the injection of a contrast agent) can be made on the skin. In one exemplary embodiment, the instrument may comprise a biopsy localization device (e.g., SeeStar) with a position sensor.

In another embodiment, a flexible mounting arm may be provided with a holder for an instrument guide (e.g., guide sleeve, instrument mounting or clamping device). The flexible mounting arm can be connected to structure such as the patient table or other adjacent equipment and may be used to hold an instrument guide during the procedure. The flexible mounting arm may be automatically robotically controllable to enable the user to determine the instrument trajectory automatically or semi-automatically, without touching the patient. Once the instrument trajectory has been finalized, the instrument may be precisely and accurately inserted into the patient. This technique may also facilitate the rapid percutaneous insertion of an instrument (e.g., by means of a biopsy cannula).

In further embodiments in which the instrument comprises a biopsy cannula, a "tracked" head (e.g., ultrasound) may be used to enable real time display of the instrument in the 3D volume (i.e., rendered or otherwise displayed on the display 26, providing a "live image" of the instrument as additional piece of information to the user.

Furthermore, when replanning of the instrument trajectory is performed, a forward-looking (i.e., "endoscopic view") may be provided to the user to enable the user to "look" into the direction of the target (see FIG. 12). Similarly, other "context-based" visualization methods may be employed, such as those which eliminate soft tissue from the 3D dataset, while retaining other elements of interest such as bones or vessels. This may enable the physician to see whether obstructions exist along the path of a planned instrument trajectory, and, furthermore, whether the path is safe (i.e., does not intersect with blood vessels). Such a 3D dataset could alternatively or additionally be acquired by means of an ultrasound head which can be movably attached on a mounting arm and "tracked."

Alternatively, a "tracked" 2D ultrasound transducer may be employed to allow the user to determine both the target and the direction of a percutaneous intervention. If the ultrasound transducer and the C-arm are registered with each other, the ultrasound path can be imported into the display, and used to orient the C-arm.

It will be appreciated that if the x-ray guidance technique is used to guide the instrument, the projection of the "skin entry point" and the "target point" does not impinge on the center of the detector 22 but rather on an outer region of the detector which cannot be shielded by a central collimator (if one is used). To alleviate this, the table 20 may be moved in such a manner that the "bull's eye view" passes through the central collimating opening.

The system may additionally employ a limitation on potential C-arm trajectories to ensure that the C-arm will not collide with the user. For example, when using the x-ray guidance procedure, the user may move from the "bull's eye view" into first and second progression views to check the position of the inserted instrument within the patient (see FIG. 14). In such cases, it may not be possible to determine whether moving the C-arm to obtain those progression views will cause a collision between the C-arm and the user. This uncertainty factor can be avoided by limiting the direction of motion of the C-arm during interventions in such a manner that rotations around the patient are carried out along the median plane (i.e., at a cranial/caudal (CRAN/CAUD) angle of 0 degree). Thus, when moving the C-arm from one position to another, the angulation of the C-arm would first be retracted (in CRAN/CAUD direction), a new angle of rotation would be targeted (in left anterior oblique/right anterior oblique (LAO/RAO) direction), and the new angulation set. This eliminates the risk that a C-arm could collide with the leg of the user since he would know what movement to expect.

In a further embodiment, feedback-controlled laser orientation technique can also be employed. In this embodiment, an additional signal (in addition to the optical signal on the screen, given by the superimposition of certain markers) is provided to the system to provide feedback as to how accurately a planned instrument trajectory coincides with the optical axis of the system (i.e., the direction of the laser).

Other user-feedback techniques may also be used, such as displaying on the display 26 offsets (in degree or distance) between the planned instrument trajectory and the optical axis of the system. Alternatively, a lamp may be provided, the color of which changes as the two are more closely aligned. Acoustic signals and haptic force feedback are other examples of acceptable feedback techniques. If such a feedback is available, the workflow could be as follows: at the beginning of the procedure, the C-arm is moved into a "generalized bull's eye view." A "generalized bull's eye view" is an x-ray view projecting target and skin entry points onto each other along an x-ray beam direction that does not coincide with the central ray of the x-ray cone. If work with the laser is desired, the table can be manually moved until the patient is in such a position that the C-arm can be moved into a viewing direction in which the axis of the optical system intersects the target point. Only after the patient and the C-arm are moved into the correct positions does the laser turn on. In all other cases, it will not. If the C-arm is moved manually, "force feedback" can be used to ensure that the positions can be approached in a controlled manner, without overshooting them. Alternatively, positioning motors may be provided to enable the table to be automatically moved into a position suitable for laser operation.

The method described herein may be automated by, for example, tangibly embodying a program of instructions upon a computer readable storage media capable of being read by machine capable of executing the instructions. A general purpose computer is one example of such a machine. A non-limiting exemplary list of appropriate storage media well known in the art would include such devices as a readable or writeable CD, flash memory chips (e.g., thumb drives), various magnetic storage media, and the like.

The features of the method have been disclosed, and further variations will be apparent to persons skilled in the art. All such variations are considered to be within the scope of the appended claims. Reference should be made to the appended claims, rather than the foregoing specification, as indicating the true scope of the disclosed method.

The functions and process steps herein may be performed automatically or wholly or partially in response to user command. An activity (including a step) performed automatically is performed in response to executable instruction or device operation without user direct initiation of the activity.

The systems and processes of FIGS. 1-20 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The processes and applications may, in alternative embodiments, be located on one or more (e.g., distributed) processing devices accessing a network linking the elements of FIGS. 1 and 5-10. Further, any of the functions and steps provided in FIGS. 18A-20 may be implemented in hardware, software or a combination of both and may reside on one or more processing devices located at any location of a network linking the elements of FIGS. 1 and 5-10 or another linked network, including the Internet.

What is claimed is:

1. A method for planning a percutaneous procedure for use in a system comprising an imaging system having a movable arm, an x-ray source and an x-ray detector mounted on the arm and a display and a system controller connected to and in communication with the imaging system and display, comprising:
   providing a three-dimensional image data set of a patient tissue region;
   obtaining an x-ray image of the patient tissue region using the x-ray source and the x-ray detector;
   co-registering the three-dimensional image data set to the x-ray image acquired using the x-ray source and the x-ray detector;
   obtaining a planned instrument trajectory within the co-registered three-dimensional image data set and x-ray image based on target point data representative of a target object within the patient tissue region and a skin entry point data representative of a skin entry point; and
   selecting by the system one of a plurality of instrument guidance procedures for aligning an instrument along the planned instrument trajectory in response to the planned instrument trajectory and a position of the movable arm;
   wherein the plurality of instrument guidance procedures comprises a laser guided procedure, an x-ray guided procedure, and a procedure that replans the instrument trajectory.

2. The method of claim 1, wherein the laser-guided procedure is selected if a central ray of the x-ray source coincides with the planned instrument trajectory.

3. The method of claim 1, wherein the x-ray guided procedure is selected if a central ray of the x-ray source does not coincide with the planned instrument trajectory, and an extension of the planned instrument trajectory intersects with the x-ray detector.

4. The method of claim 1, wherein the instrument trajectory is replanned if a central ray of the x-ray source does not coincide with the planned instrument trajectory and an extension of the planned instrument trajectory does not intersect with the x-ray detector.

5. The method of claim 4, further comprising a warning signal to a user when a central ray of the x-ray source does not coincide with the planned instrument trajectory and an extension of the planned instrument trajectory does not intersect with the x-ray detector.

6. The method of claim 1, wherein replanning the instrument trajectory comprises manually replanning the instrument trajectory using a graphical user interface.

7. The method of claim 1, wherein replanning the instrument trajectory comprises automatically replanning the instrument trajectory.

8. The method of claim 1, wherein the co-registering step comprises applying a transform to the 3-dimensional image data set such that points in a resulting overlay image align with counterpart points in the x-ray image.

9. The method of claim 1, wherein the step of aligning an instrument comprises aligning the instrument along a laser beam path generated by a laser pointer, the laser beam path intersecting the skin entry point and the target object.

10. The method of claim 9, wherein the laser beam path comprises the intersection of at least two laser fan patterns.

11. The method of claim 1, wherein the step of obtaining an x-ray image of the patient tissue region using the x-ray source and the x-ray detector comprises obtaining a plurality of x-ray images, displaying the plurality of x-ray images on the display along with a three-dimensional rendering of the three-dimensional image data set, and an overlay image representing a 2-dimensional rendering of the 3-dimensional image data set.

12. The method of claim 11, wherein the skin entry point, the target point and the planned instrument trajectory are graphically displayed in their respective positions on the plurality of displayed x-ray images, the three-dimensional rendering and the overlay image.

13. A method for planning a percutaneous procedure comprising the activities of:
   employing an imaging system having a movable arm, an x-ray source and an x-ray detector mounted on the arm and a display and a system controller connected to and in communication with the imaging system and display, and a machine-readable storage medium encoded with a computer program code such that, when the computer program code is executed by at least one processor in the imaging system, the at least one processor performs a method including,
   providing a three-dimensional image data set of a patient tissue region;
   obtaining an x-ray image of the patient tissue region using the x-ray source and the x-ray detector;
   co-registering the three-dimensional image data set to the x-ray image acquired using the x-ray source and the x-ray detector;
   obtaining a planned instrument trajectory within the co-registered three-dimensional image data set and x-ray image based on target point data representative of a target object within the patient tissue region and a skin entry point data representative of a skin entry point; and
   selecting by the system one of a plurality of instrument guidance procedures for aligning an instrument along the planned instrument trajectory in response to the planned instrument trajectory and a position of the movable arm;
   wherein the plurality of instrument guidance procedures comprises a laser-guided procedure, an x-ray guided procedure, and a procedure that replans the instrument trajectory.

14. The method of claim 13, wherein the laser-guided procedure is selected if a central ray of the x-ray source coincides with the planned instrument trajectory.

15. The method of claim 13, wherein the x-ray guided procedure is selected if a central ray of the x-ray source does not coincide with the planned instrument trajectory, and an extension of the planned instrument trajectory intersects with the x-ray detector.

16. The method of claim 13, wherein the instrument trajectory is replanned if a central ray of the x-ray source does not coincide with the planned instrument trajectory and an extension of the planned instrument trajectory does not intersect with the x-ray detector.

17. The method of claim 16, further comprising a warning signal to a user when a central ray of the x-ray source does not coincide with the planned instrument trajectory and an extension of the planned instrument trajectory does not intersect with the x-ray detector.

18. The method of claim 13, wherein replanning the instrument trajectory comprises manually replanning the instrument trajectory using a graphical user interface.

19. The method of claim 13, wherein replanning the instrument trajectory comprises automatically replanning the instrument trajectory.

20. The method of claim 13, wherein the co-registering step comprises applying a transform to the 3-dimensional image data set such that points in a resulting overlay image align with counterpart points in the x-ray image.

21. The method of claim 13, wherein the step of aligning an instrument comprises aligning the instrument along a laser beam path generated by a laser pointer, the laser beam path intersecting the skin entry point and the target object.

22. The method of claim 21, wherein the laser beam path comprises the intersection of at least two laser fan patterns.

23. The method of claim 13, wherein the step of obtaining an x-ray image of the patient tissue region using the x-ray source and the x-ray detector comprises obtaining a plurality of x-ray images, displaying the plurality of x-ray images on the display along with a three-dimensional rendering of the three-dimensional image data set, and an overlay image representing a 2-dimensional rendering of the 3-dimensional image data set.

24. The method of claim 23, wherein the skin entry point, the target point and the planned instrument trajectory are graphically displayed in their respective positions on the plurality of displayed x-ray images, the three-dimensional rendering and the overlay image.

* * * * *